US007871775B2

(12) United States Patent
Clark et al.

(10) Patent No.: US 7,871,775 B2
(45) Date of Patent: Jan. 18, 2011

(54) COMPOSITIONS AND METHODS FOR THE IDENTIFICATION, ASSESSMENT, PREVENTION AND THERAPY OF HUMAN CANCERS

(75) Inventors: Edwin Clark, Ashland, MA (US); Tallessyn Grenfell-Lee, Cambridge, MA (US); Karen Lu, Houston, TX (US); Lynn Hartmann, Rochester, MN (US); Jeffrey L. Brown, Arlington, MA (US); Robert C. Bast, Jr., Houston, TX (US); Gordon B. Mills, Houston, TX (US)

(73) Assignees: Millennium Pharmaceuticals, Inc, Cambridge, MA (US); Mayo Foundation for Medical Edication and Research, Rochester, MN (US); Board of Regents, The University of Texas System, Austin, TX (US)

( * ) Notice: Subject to any disclaimer, the term of this patent is extended or adjusted under 35 U.S.C. 154(b) by 250 days.

(21) Appl. No.: 12/002,783

(22) Filed: Dec. 17, 2007

(65) Prior Publication Data
US 2008/0286780 A1   Nov. 20, 2008

Related U.S. Application Data

(63) Continuation of application No. 10/071,510, filed on Feb. 8, 2002, now Pat. No. 7,338,758.

(60) Provisional application No. 60/267,276, filed on Feb. 8, 2001.

(51) Int. Cl.
  *C12Q 1/68* (2006.01)
(52) U.S. Cl. .......................................... 435/6; 536/23.1
(58) Field of Classification Search ..................... 435/6; 536/23.1
  See application file for complete search history.

(56) References Cited

U.S. PATENT DOCUMENTS

| 7,338,758 B2 | 3/2008 | Clark et al. |
| 2003/0143552 A1 | 7/2003 | Clark et al. |

OTHER PUBLICATIONS

Selvanayagam et al. (Cancer Gen. Cytogen. 2004; 154: 63-66).*
Sakamoto et al. (Hum. Cell. Dec. 2001; 14 (4): 305-315).*
Huang et al. (Mol. Cancer Ther. Aug. 2002; 1: 769-776).*
Lavarino et al. (J. Clin. Oncol. Dec. 2000; 18 (23): 3936-3945).*
Bonaldo et al., "Normalization and subtraction: two approaches to facilitate gene discovery", *Genome Res.*, 6:791-806 (1996).
Hartley et al., "DNA cloning using in vitro site-specific recombination", *Genome Res.*, 10:1788-1795 (2000).
Nagase et al., "Prediction of the coding sequences of unidentified human genes. Xx. The complete sequences of 100 new cDNA clones from brain which code for large proteins in vitro", *DNA Research*, 8:85-95 (2001).
Simpson et al., "Systematic subcellular localization of novel proteins identified by large-scale cDNA sequencing", *EMBO Reports*, 11(31):287-292 (2000).
Wiemann et al., "Toward a catalog of human genes and proteins: sequencing and analysis of 500 novel complete protein coding human cDNAs", *Genome Res.*, 11:422-435 (2001).
GenBank Accession No. NT_030059, Jun. 10, 2009.
GenBank Accession No. NM_032439, Mar. 4, 2010.
Swiss-Prot Accession No. Q96FC7, Apr. 20, 2010.
Genbank Accession No. BAB47425.1, Jun. 5, 2001.
GenBank Accession No. NP_115815, Mar. 4, 2010.
GenBank Accession No. NP_001137246, Mar. 4, 2010.
GenBank Accession No. NM_001143774, Mar. 4, 2010.
GenBank Accession No. AC_025038, Apr. 9, 2002.

* cited by examiner

*Primary Examiner*—Stephen L Rawlings
(74) *Attorney, Agent, or Firm*—McCarter & English, LLP; Maria Laccotripe Zacharakis; Alexandra Jones

(57) ABSTRACT

The present invention is directed to the identification of markers that can be used to determine whether tumors are sensitive or resistant to a therapeutic agent. The present invention is also directed to the identification of therapeutic targets. The invention features a number of "sensitivity markers." These are markers that are expressed in most or all cell lines that are sensitive to treatment with an agent and which are not expressed (or are expressed at a rather low level) in cells that are resistant to treatment with that agent. The invention also features a number of "resistance markers." These are markers that are expressed in most or all cell lines that are resistant to treatment with an agent and which are not expressed (or are expressed at a rather low level) in cells that are sensitive to treatment with that agent. The invention also features marker sets that can predict patients that are likely to respond or not to respond to an agent.

4 Claims, No Drawings

SEQUENCE LISTING

<160> NUMBER OF SEQ ID NOS: 19

<210> SEQ ID NO 1
<211> LENGTH: 242
<212> TYPE: DNA
<213> ORGANISM: Homo sapiens
<220> FEATURE:
<221> NAME/KEY: misc_feature
<222> LOCATION: 57, 62, 71, 78, 117, 133, 137, 207, 219, 226, 229
<223> OTHER INFORMATION: n = A,T,C or G

<400> SEQUENCE: 1

```
aggtacaagc tttttttttt tttttttttt tttttttttt tcctactgga atcgttnaat      60
gngtctactt nttccacnca taattataaa agaataagaa tcgacaaaaa tattttnttt     120
ccataatatg tanaggnggt tggtttcttt tttttttttt ttcttttctt ttaactttt      180
```

```
tttttttttt tttttttttt gggctcnaaa gggggtagng ggggtnctnt aggacctgcc       240
cg                                                                      242

<210> SEQ ID NO 2
<211> LENGTH: 417
<212> TYPE: DNA
<213> ORGANISM: Homo sapiens
<220> FEATURE:
<221> NAME/KEY: misc_feature
<222> LOCATION: 338, 349, 388
<223> OTHER INFORMATION: n = A,T,C or G

<400> SEQUENCE: 2
tttatgagaa agcagctatt aaaggtagag tgattcaagt ctataaggca atttatattc        60
tatatttagt ttttcattct gaatagactg aaaaaatata tgaattagaa atttatttaa       120
gaccatcttt cttttgttgc ttttttttaaa catttacttt tctttaagcc ataaggatgc      180
ataaattata cagggcatga ccttatgagt aacatcaaca ggtatttcag aaataacaga      240
acacgtctag aaatgtatgg tggtaatatt aatctataca ttttttggca tgatttgtac      300
attgacattg tatgaaatga gcacactgag ggttttttngg tggtactgnc gcatccaagg     360
aggttgggga gaactatata agaatgtntt ataatcacta ttttaaataa agtaaaa         417

<210> SEQ ID NO 3
<211> LENGTH: 512
<212> TYPE: DNA
<213> ORGANISM: Homo sapiens

<400> SEQUENCE: 3
cgtgactgag gacagtgaaa agagcccacc tggtgtagag tgctcatttt agctgccaag       60
aaaagcctaa tttattttca gggcaaaact tctgcactgg gacaaatgtc ttcattataa      120
tccaaaagca gcatcaggaa aagaagctga actgtgcgaa tagaaatgaa tggggctgct     180
gctgctgctg ctgctttctt tttaatcagt agaaatggaa ttctgcctgc caaacagaag     240
tctaggagga acctgcagac ggcccctgta ctgagggcat tttgtcaggg cttaaagcaa     300
ccttcaagat catgacactc tgctatgagg accgaaagaa cttggagata aatatacatg     360
tactatgtgg tgggaccgat tttgaatctg aactaaatta aatgatggaa aacgaccttg     420
ggtgagttca ttcatggctg aacttgctgg gaatgataca acttttcaaa ataatttgtt    480
tccttcaaat gacaccaaca cctatagtta ag                                   512

<210> SEQ ID NO 4
<211> LENGTH: 356
<212> TYPE: DNA
<213> ORGANISM: Homo sapiens
<220> FEATURE:
<221> NAME/KEY: misc_feature
<222> LOCATION: 1, 17, 24, 39, 95, 98, 113, 116, 130, 143, 153, 154,
      155, 164, 165, 172, 174, 190, 192, 198, 202, 206, 207, 238, 245,
      246, 247, 253, 285, 295, 299, 300, 302, 338
<223> OTHER INFORMATION: n = A,T,C or G

<400> SEQUENCE: 4
ncggttgaac tacgganaac aacncgctgc cttcacagna cctagagtct cctttggagc       60
taccaacctc gccgaaggta cggcgacaca gacgngangt gtacaagctt ttntanatgg      120
tggatattcn acaattaaat tcntacgtac tcnnngtcca gtcnngagtc cnantgagct      180
gtttgctaan tnatgaantt cnttcnngca cgtgaagggc aaagagaaat aagggccnac     240
ttccnnnaag ggnttcctcg cgcatttagg tatcaggctt acttnagtat gtatngccnn     300
```
cntccgagcg ggagagccaa gggtgtcgta taaaattnaa aggaataaca taaaaa      356

<210> SEQ ID NO 5
<211> LENGTH: 577
<212> TYPE: DNA
<213> ORGANISM: Homo sapiens
<220> FEATURE:
<221> NAME/KEY: misc_feature
<222> LOCATION: 53, 58, 59, 143, 173, 197, 242, 303, 432, 491, 504, 514,
      537
<223> OTHER INFORMATION: n = A,T,C or G

<400> SEQUENCE: 5
gtcgaccccg cgtccgctta gggaactgca atattataag tatagtaatg acngcagnng       60
agaaccataa tgatggcctc cccggcaaag aagaaccaac ccgtgttacg cctgaggttg      120
caattttttg aattttgca gtnagaccct ggcgatgacc ttgagcagta ggngataaat      180
tccacatgct tagcgtncca gtaatggaac actaggcata aatgggttat taaagtatcc      240
anaattaaca tgcttagctg tgacattgga aaggcaatgt gtttgctgtg cacacatac      300
tantaaataa tgactggtcc gaatttggtt ttcgtttgtc tattaaagtc aatttactaa      360
ggcagggagg gcccagagct gtgctgtcca gttcaatagc catgcgtgac tgctaaggac      420
ttccaaagtg gntagtccaa tgtcaggtat gctgcaagtg tcaaacacac actggatttc      480
aaagactaaa nccaaaaaaa tgtnaaatca tctnaatatt ttggttatac tcggttnaag      540
aaaataaaat tattttttgcc ttttatgttt ttaaaag                              577

<210> SEQ ID NO 6
<211> LENGTH: 331
<212> TYPE: DNA
<213> ORGANISM: Homo sapiens
<220> FEATURE:
<221> NAME/KEY: misc_feature
<222> LOCATION: 3
<223> OTHER INFORMATION: n = A,T,C or G

<400> SEQUENCE: 6
ggncaccaca ctctacaaag gcagtcaact acatgacaca ttccgcttct gcctggtcac       60
caacttgacg atggactccg tgttggtcac tgtcaaggca ttgttctcct ccaatttgga      120
ccccagcctg gtggagcaag tctttctaga taagaccctg aatgcctcat tccattggct      180
gggctccacc taccagttgg tggacatcca tgtgacagaa atggagtcat cagtttatca      240
accaacaagc agctccagca cccagcactt ctacctgaat ttcaccatca ccaacctacc      300
atattcccag gacaaagccc agccaggcac c                                     331

<210> SEQ ID NO 7
<211> LENGTH: 446
<212> TYPE: DNA
<213> ORGANISM: Homo sapiens

<400> SEQUENCE: 7
ccctcgcggt ggcgggcgag gtgcatcacc ctgctgaggg acatccagga caaggtcacc       60
acactctaca aaggcagtca actacatgac acattccgct tctgcctggt caccaacttg      120
acgatggact ccgtgttggt cactgtcaag gcattgttct cctccaattt ggaccccagc      180
ctggtggagc aagtctttct agataagacc ctgaatgcct cattccattg gctgggctcc      240
acctaccagt tggtggacat ccatgtgaca gaaatggagt catcagttta tcaaccaaca      300
agcagctcca gcacccagca cttctacctg aatttcacca tcaccaacct accatattcc      360
caggacaaag cccagccagg caccaccaat taccagagga acaaaaggaa tattgaggat            420
gcgctcaacc aactcttcga aacagc                                                446

<210> SEQ ID NO 8
<211> LENGTH: 497
<212> TYPE: DNA
<213> ORGANISM: Homo sapiens
<220> FEATURE:
<221> NAME/KEY: misc_feature
<222> LOCATION: 497
<223> OTHER INFORMATION: n = A,T,C or G

<400> SEQUENCE: 8
tacttagggc gaattggagc tccccgcggt ggcggccgag gtacgcggga gataagaccc            60
tgaatgcctc attccattgg ctgggctcca cctaccagtt ggtggacatc catgtgacag           120
aaatggagtc atcagtttat caaccaacaa gcagctccag cacccagcac ttctacctga           180
atttcaccat caccaaccta ccatattccc gggacaaagc ccagccaggc accaccaatt           240
accagaggaa caaaggaat attgaggatg cgctcaacca actcttccga aacagcagca            300
tcaagagtta ttttttctgac tgtcaagttt caacattcag gtctgtcccc aacaggcacc         360 acaccgggt ggactccctg tgtaacttct cgccactggc tcggagagta gacagagttg            420
ccatctatga ggaatttctg cggatgaccc ggaatgggta cctgcccggg ccggccgctt           480
cggctttaga actagtn                                                          497

<210> SEQ ID NO 9
<211> LENGTH: 488
<212> TYPE: DNA
<213> ORGANISM: Homo sapiens
<220> FEATURE:
<221> NAME/KEY: misc_feature
<222> LOCATION: 27
<223> OTHER INFORMATION: n = A,T,C or G

<400> SEQUENCE: 9
atagggcgaa ttggagctcc ccgcggnggc ggccgaggta ccattccggg tcatccgcag            60
aaattcctca tagatggcaa ctctgtctac tctccgagcc agtggcgaga agttacacag           120
ggagtccacc ccgtgtggt gcctgttggg gacagacctg aatgttgaaa cttgacagtc            180
agaaaaataa ctcttgatgc tgctgtttcg gaagagttgg ttgagcgcat cctcaatatt          240
ccttttgttc ctctggtaat tggtggtgcc tggctgggct ttgtcctggg aatatggtag          300
gttggtgatg gtgaaattca ggtagaagtg ctgggtgctg gagctgcttg ttggttgata          360
aactgatgac tccattttctg tcacatggat gtccaccaac tggtaggtgg agccagcca           420 atgggaatga ggcattcagg gtcttatcta gaaagacttg ctccaccagg ctggggtcca          480
aattggag                                                                    488

<210> SEQ ID NO 10
<211> LENGTH: 463
<212> TYPE: DNA
<213> ORGANISM: Homo sapiens

<400> SEQUENCE: 10
ccgcggtggc ggccgcccgg gcaggtacat caccctgctg agggacatcc aggacaaggt            60
caccacactc tacaaaggca gtcaactaca tgcacattc cgcttctgcc tggtcaccaa           120
cttgacgatg gactccgtgt cggtcactgt caaggcattg ttctcctcca atttggaccc           180

```
cagcctggtg gagcaagtct ttctagataa gaccctgaat gcctcattcc attggctggg      240
ctccacctac cagttggtgg acatccatgt ggcagaaatg gagtcatcag tttatcaacc      300
aacaagcagc tccagcaccc agcacttcta cctgaatttc accatcacca acctaccata      360
ttcccaggac aaagcccagc caggcaccac caattaccag aggaacaaaa ggaatattga      420
ggatgcgctc aaccaactct ccgaaacag cagcatcaag agt                         463
```

<210> SEQ ID NO 11
<211> LENGTH: 302
<212> TYPE: DNA
<213> ORGANISM: Homo sapiens
<220> FEATURE:
<221> NAME/KEY: misc_feature
<222> LOCATION: 6, 52, 53
<223> OTHER INFORMATION: n = A,T,C or G

<400> SEQUENCE: 11

```
accgcngtgg cggccgcccg ggcaggtaca tcaccctgct gagggacttt tnnggacaag       60
gtcaccacac tctacaaagg cagtcaacta catgacacat tccgcttctg cctggtcacc      120
aacttgacga tggactccgt gttggtcact gtcaaggcat tgttctcctc caatttggac      180
cccagcctgg tggagcaagt cttttctagat aagaccctga atgcctcatt ccattggctg      240
ggctccacct accagttggt ggacatccat gtgacagaaa tggagtcatc agttttatca      300
ac                                                                     302
```

<210> SEQ ID NO 12
<211> LENGTH: 534
<212> TYPE: DNA
<213> ORGANISM: Homo sapiens
<220> FEATURE:
<221> NAME/KEY: misc_feature
<222> LOCATION: 18, 463, 474, 518
<223> OTHER INFORMATION: n = A,T,C or G

<400> SEQUENCE: 12

```
agggcgaatt ggagctcncc gcggtggcgg ccgaggtacc acctgaaggc cctcacactc       60
aacttcacca tctccaatct ccagtattca ccagatatgg gcaagggctc agctacattc      120
aactccaccg aggggggtcct tcagcacctg ctcagaccct tgttccagaa gagcagcatg      180
ggccccttct acttgggttg ccaactgatc tccctcaggc ctgagaagga tggggcagcc      240
actggtgtgg acaccacctg cacctaccac cctgaccctg tgggcccccgg gctggacata      300 cagcagcttt actgggagct gagtcagctg acccatgggt gtcacccaac tgggcttcta      360
ttgtcctgga cagggatagc ctcttcatca atggctatgc accccaaaat ttatcaatcc      420
gggggcgagg tacctgcccc gggcgggccg cttaaaacta ggngggatcc ccnggcttg      480 caggaatttc gatattcaag cttatcgata cccgtccnac cttcgagggg gggg            534
```

<210> SEQ ID NO 13
<211> LENGTH: 290
<212> TYPE: DNA
<213> ORGANISM: Homo sapiens
<220> FEATURE:
<221> NAME/KEY: misc_feature
<222> LOCATION: 15, 16, 39, 41, 71, 106, 129, 137, 140, 149, 164, 167,
       226, 245, 251, 263, 268
<223> OTHER INFORMATION: n = A,T,C or G

<400> SEQUENCE: 13

```
tgggggaaag ggagnnccca acgatcctgg aactttaant ntggaaagag tgagattcag       60
```

```
aaatcgccac nactggactt taagggacgt cctgtgtcag cacaanggac tggcacacac    120
agacacacna gaccgangan aaactgcana caaatggaga tacnaanact tagaaggaca    180
gctcctttca cctcatccta cttgtccaga aggtaaaaag acacanccag aaagaaaagg    240
catcngctca nctctcagat cangacangc tgtggatctg tggcggtact              290
```

<210> SEQ ID NO 14
<211> LENGTH: 430
<212> TYPE: DNA
<213> ORGANISM: Homo sapiens
<220> FEATURE:
<221> NAME/KEY: misc_feature
<222> LOCATION: 93, 315, 407
<223> OTHER INFORMATION: n = A,T,C or G

<400> SEQUENCE: 14

```
gcgtccgaat tcctgggta ccccgtatat aagaaaatgt taaagtcagg caggaaaact    60
atagaattaa agccttatag tatattatat agnaaagccc tatatagtat agacagaaaa    120
gtttagggaa ggcccacaat tgcaaagaaa agtggtggtc acggaacaag ggaatgtcat    180
acaaatgtgg acacacactg cgttactgag cgccacgtct cataggtgag aagcataact    240
ctagaaggtg agaaatgaga attttcactt ccatccttcc atttgttgtg tgactctgcc    300
atttactttc ctttnttttg tattttcatt ttccttttaa aaatgaaat atgaattttg     360 aatttctgct ctatctcaca ggttttttgt ggggatgcat ttaaaangtt taattagtaa    420
ataatggtat                                                          430
```

<210> SEQ ID NO 15
<211> LENGTH: 435
<212> TYPE: DNA
<213> ORGANISM: Homo sapiens
<220> FEATURE:
<221> NAME/KEY: misc_feature
<222> LOCATION: 39, 242, 363, 393, 404, 406, 412
<223> OTHER INFORMATION: n = A,T,C or G

<400> SEQUENCE: 15

```
ccaaactatt tggacagaat ggcttcaaaa gctaggcgna aatgttcaca ttataaaaag    60
ttaaatatta ccttcaatac ctgtcagtag cctactgaca aattatgact aaacaaaggt    120
atttgtatga ctatgtaata gatcatccgc tgaaaagtaa aacaaaataa caaaaaaact    180
tgtcctaatg ggaaagcatg cttaataaaa ggaaatgcac gaagttataa acatgttttg    240
tnagtaagta ttcagaatta aaattatgtg atacattttt atgattgctt aatgatcctt    300
ggatgtcaga ttccttgggt ctatttatag ctaaattata atgaaaaatt caaggcttgc    360
tgnagcaact ctgtcaacaa atatattagt ttngcttata tatntngatt cnttatgtgg    420
gaaaaattac taccc                                                    435
```

<210> SEQ ID NO 16
<211> LENGTH: 493
<212> TYPE: DNA
<213> ORGANISM: Homo sapiens

<400> SEQUENCE: 16

```
cggccggccc ggggatgcc gagtcccaag aggccgagtt tgagaggctg gtggcagaat    60
tcccggagaa ggaggcccag ctgtccctgg tggaagcgca gggctggctg gtgatggaga    120
agtcttctcc ggagggtgct gccgtggtgc aggaggagc cagggagctg gcagagtcgt    180
ggcgggcctt gaggctgctg aagaaagtc tgctgagcct catcagaaac tggcatctgc    240
```

```
agaggatgga agtggattcg gggaagaaaa tggttttcac caacaacatc ccaaagtcag      300
gatttctcat caatcccatg gatcctattc ccaggcatcg tcgacgcgtg agtctgtcta      360
gcagggctgt gggagaaggg gccaggcccc aggtcaagag gtgggtaggg gtctccagca      420
caggcccctc cctgtctggg gcaacatgct ctgctctgag gacttggcca cgtcctgtct      480
catttgagcc tgc                                                         493

<210> SEQ ID NO 17
<211> LENGTH: 315
<212> TYPE: DNA
<213> ORGANISM: Homo sapiens

<400> SEQUENCE: 17
gcgtccggtt acaaagtcag gttgttatgg tttgcatgac tttgagaagc tagtggaatg       60
gaaataaagt taggagcagc aggaggaggc tctgtgtggg cacatctcct tcagggcat      120 ggtactgttc atggacagag gaagtcctat ggcatatgct gggacagaca gtgaagggta      180
ggtcttacaa agaggcttta cgttagagta taataatcac ttatctgtat gcatctatga      240
atgatctcac cggatgtgaa gaatatgtat tttttaaaaac agcatgaaac ggcctgtaat      300
cccagtactt ttggg                                                       315

<210> SEQ ID NO 18
<211> LENGTH: 339
<212> TYPE: DNA
<213> ORGANISM: Homo sapiens

<400> SEQUENCE: 18
acttattgaa tcatcgaatt cattgaagtt tggctccaac ctatcatatc gccgatgttt       60 acttttcct attcttcata aagttctaaa ttcagaatgt gaggtggaca aattcatttc      120
agttccacaa gtggtagcat ttaaatatca gcagcttaag tattcaaaat taatagattg      180 cattttttaaa atggtgaaat tctgacagtt tgcagggaaa aggtgctgaa tatcttgata      240
taatttacat acttctataa acaggcattt ttatacccttt ggaaagataa atgagtagaa      300
accaagtatt ttacaattct aatagttata ctgacatgt                             339

<210> SEQ ID NO 19
<211> LENGTH: 520
<212> TYPE: DNA
<213> ORGANISM: Homo sapiens

<400> SEQUENCE: 19
tccgctaaaa atttgttcgg gcctttggct taattcagag atctgcccat ggggttctat       60
tactttgctc tttaactttg ttcgatcctt cttggatcag tcttgcaatt cattcttgtc      120
ttttcctgaa taacatctat gttttgcccct cttttgagtg ctatcttaat atgccagcct      180
atttctacct ttcttgtgca gggtagcata atttttactt tccattatac ctcagtccca      240
caccttgttg tctgttttatt tcaataccta agatacttat cctcagttcc tagcttactt      300
tagttctgaa agttggatat ccataattgt agtggtctta aatctgtaaa acacatatgg      360
atgggaaacc actgaataat gtaaataaat atgaataacg atgataaaat aaaaatgata      420
aaaataactg agttcaatga tattaaaaac ataagtcagt ttaactattt tttttttgag      480
acaggggctc tgtcaccaag gctagagctg cagtgagtca                            520
```

COMPOSITIONS AND METHODS FOR THE IDENTIFICATION, ASSESSMENT, PREVENTION AND THERAPY OF HUMAN CANCERS

RELATED APPLICATIONS

This application is a continuation of U.S. application Ser. No. 10/071,510, filed Feb. 8, 2002, issued as U.S. Pat. No. 7,338,758, which claims priority to U.S. Provisional Application No. 60/267,276 filed on Feb. 8, 2001. The entire contents of each of the foregoing applications are incorporated herein by reference.

BACKGROUND OF THE INVENTION

Cancers can be viewed as a breakdown in the communication between tumor cells and their environment, including their normal neighboring cells. Growth-stimulatory and growth-inhibitory signals are routinely exchanged between cells within a tissue. Normally, cells do not divide in the absence of stimulatory signals or in the presence of inhibitory signals. In a cancerous or neoplastic state, a cell acquires the ability to "override" these signals and to proliferate under conditions in which a normal cell would not.

In general, tumor cells must acquire a number of distinct aberrant traits in order to proliferate in an abnormal manner. Reflecting this requirement is the fact that the genomes of certain well-studied tumors carry several different independently altered genes, including activated oncogenes and inactivated tumor suppressor genes. In addition to abnormal cell proliferation, cells must acquire several other traits for tumor progression to occur. For example, early on in tumor progression, cells must evade the host immune system. Further, as tumor mass increases, the tumor must acquire vasculature to supply nourishment and remove metabolic waste. Additionally, cells must acquire an ability to invade adjacent tissue. In many cases cells ultimately acquire the capacity to metastasize to distant sites.

It is apparent that the complex process of tumor development and growth must involve multiple gene products. It is therefore important to define the role of specific genes involved in tumor development and growth and identify those genes and gene products that can serve as targets for the diagnosis, prevention and treatment of cancers.

In the realm of cancer therapy it often happens that a therapeutic agent that is initially effective for a given patient becomes, over time, ineffective or less effective for that patient. The very same therapeutic agent may continue to be effective over a long period of time for a different patient. Further, a therapeutic agent that is effective, at least initially, for some patients can be completely ineffective or even harmful for other patients. Accordingly, it would be useful to identify genes and/or gene products that represent prognostic genes with respect to a given therapeutic agent or class of therapeutic agents. It then may be possible to determine which patients will benefit from particular therapeutic regimen and, importantly, determine when, if ever, the therapeutic regime begins to lose its effectiveness for a given patient. The ability to make such predictions would make it possible to discontinue a therapeutic regime that has lost its effectiveness well before its loss of effectiveness becomes apparent by conventional measures.

SUMMARY OF THE INVENTION

The present invention is directed to the identification of markers that can be used to determine the sensitivity or resistance of tumors to a therapeutic agent. By examining the expression of one or more of the identified markers, whose expression correlates with sensitivity to a therapeutic agent or resistance to a therapeutic agent, in a sample of tumor cells, it is possible to determine whether a therapeutic agent or combination of agents will be most likely to reduce the growth rate of the tumor cells and can further be used in selecting appropriate treatment agents. The markers of the present invention whose expression correlates with sensitivity or with resistance to an agent are listed in Tables 1-6.

By examining the expression of one or more of the identified markers in a tumor, it is possible to determine which therapeutic agent or combination of agents will be most likely to reduce the growth rate of the tumor. By examining the expression of one or more of the identified markers in a tumor, it is also possible to determine which therapeutic agent or combination of agents will be the least likely to reduce the growth rate of the tumor. By examining the expression of one or more of the identified markers, it is therefore possible to eliminate ineffective or inappropriate therapeutic agents. Moreover, by examining the expression of one or more of the identified markers in a tumor sample taken from a patient during the course of therapeutic treatment, it is possible to determine whether the therapeutic treatment is continuing to be effective or whether the tumor has become resistant (refractory) to the therapeutic treatment. It is also possible to identify new anti-cancer agents by examining the expression of one or more markers when tumor cells are exposed to a potential anti-cancer agent. Importantly, these determinations can be made on a patient by patient basis or on an agent by agent (or combination of agents) basis. Thus, one can determine whether or not a particular therapeutic treatment is likely to benefit a particular patient or group/class of patients, or whether a particular treatment should be continued.

The present invention further provides previously unknown or unrecognized targets for the development of anti-cancer agents, such as chemotherapeutic compounds. The markers of the present invention can be used as targets in developing treatments (either single agent or multiple agent) for cancer, particularly for those cancers which display resistance to agents and exhibit expression of one or more of the markers identified herein.

Other features and advantages of the invention will be apparent from the detailed description and from the claims. Although materials and methods similar or equivalent to those described herein can be used in the practice or testing of the invention, the preferred materials and methods are described below.

DETAILED DESCRIPTION OF THE INVENTION

The present invention is based, in part, on the identification of markers that can be used to determine whether a tumor is sensitive or resistant to a therapeutic agent. Based on these identifications, the present invention provides, without limitation: 1) methods for determining whether a therapeutic agent (or combination of agents) will or will not be effective in stopping or slowing tumor growth; 2) methods for monitoring the effectiveness of a therapeutic agent (or combination of agents) used for the treatment of cancer; 3) methods for identifying new therapeutic agents for the treatment of cancer; 4) methods for identifying combinations of therapeutic agents for use in treating cancer; and 5) methods for identifying specific therapeutic agents and combinations of therapeutic agents that are effective for the treatment of cancer in specific patients.

Definitions

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described herein. All publications, patent applications, patents, and other references mentioned herein are incorporated by reference in their entirety. The content of all GenBank database records cited throughout this application (including the Tables) are also hereby incorporated by reference. In the case of conflict, the present specification, including definitions, will control. In addition, the materials, methods, and examples are illustrative only and are not intended to be limiting.

The articles "a" and "an" are used herein to refer to one or to more than one (i.e. to at least one) of the grammatical object of the article. By way of example, "an element" means one element or more than one element.

A "marker" is a naturally-occurring polymer corresponding to at least one of the nucleic acids listed in Tables 1-6. For example, markers include, without limitation, sense and antisense strands of genomic DNA (i.e. including any introns occurring therein), RNA generated by transcription of genomic DNA (i.e. prior to splicing), RNA generated by splicing of RNA transcribed from genomic DNA, and proteins generated by translation of spliced RNA (i.e. including proteins both before and after cleavage of normally cleaved regions such as transmembrane signal sequences). As used herein, "marker" may also include a cDNA made by reverse transcription of an RNA generated by transcription of genomic DNA (including spliced RNA).

The term "probe" refers to any molecule which is capable of selectively binding to a specifically intended target molecule, for example a marker of the invention. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic monomers.

The "normal" level of expression of a marker is the level of expression of the marker in cells of a patient not afflicted with cancer.

"Over-expression" and "under-expression" of a marker refer to expression of the marker of a patient at a greater or lesser level, respectively, than normal level of expression of the marker (e.g. at least two-fold greater or lesser level).

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue-specific manner.

A "constitutive" promoter is a nucleotide sequence which, when operably linked with a polynucleotide which encodes or specifies a gene product, causes the gene product to be produced in a living human cell under most or all physiological conditions of the cell.

An "inducible" promoter is a nucleotide sequence which, when operably linked with a polynucleotide which encodes or specifies a gene product, causes the gene product to be produced in a living human cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

A "transcribed polynucleotide" is a polynucleotide (e.g. an RNA, a cDNA, or an analog of one of an RNA or cDNA) which is complementary to or homologous with all or a portion of a mature RNA made by transcription of a genomic DNA corresponding to a marker of the invention and normal post-transcriptional processing (e.g. splicing), if any, of the transcript.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

A marker is "fixed" to a substrate if it is covalently or non-covalently associated with the substrate such the substrate can be rinsed with a fluid (e.g. standard saline citrate, pH 7.4) without a substantial fraction of the marker dissociating from the substrate.

As used herein, a "naturally-occurring" nucleic acid molecule refers to an RNA or DNA molecule having a nucleotide sequence that occurs in nature (e.g. encodes a natural protein).

Expression of a marker in a patient is "significantly" higher or lower than the normal level of expression of a marker if the level of expression of the marker is greater or less, respectively, than the normal level by an amount greater than the standard error of the assay employed to assess expression, and preferably at least twice, and more preferably three, four, five or ten times that amount. Alternately, expression of the marker in the patient can be considered "significantly" higher or lower than the normal level of expression if the level of expression is at least about two, and preferably at least about three, four, or five times, higher or lower, respectively, than the normal level of expression of the marker.

Cancer is "inhibited" if at least one symptom of the cancer is alleviated, terminated, slowed, or prevented. As used herein, cancer is also "inhibited" if recurrence or metastasis of the cancer is reduced, slowed, delayed, or prevented.

A tumor, including tumor cells, is "sensitive" to a therapeutic agent if its rate of growth is inhibited as a result of contact with the therapeutic agent, compared to its growth in the absence of contact with the therapeutic agent. The quality of being sensitive to a therapeutic agent is a variable one, with different tumors exhibiting different levels of "sensitivity" to a given therapeutic agent, under different conditions. In one embodiment of the invention, tumors may be predisposed to sensitivity to an agent if one or more of the corresponding sensitivity markers are expressed.

A tumor, including tumor cells, is "resistant" to a therapeutic agent if its rate of growth is not inhibited, or inhibited to a very low degree, as a result of contact with the therapeutic agent when compared to its growth in the absence of contact with the therapeutic agent. The quality of being resistant to a therapeutic agent is a highly variable one, with different tumors exhibiting different levels of "resistance" to a given therapeutic agent, under different conditions. In another embodiments of the invention, tumors may be predisposed to resistance to an agent if one or more of the corresponding resistance markers are expressed.

A kit is any manufacture (e.g. a package or container) comprising at least one reagent, e.g. a probe, for specifically detecting a marker of the invention. The manufacture may be promoted, distributed, or sold as a unit for performing the methods of the present invention. The reagents included in such a kit comprise probes/primers and/or antibodies for use in detecting sensitivity and resistance gene expression. In addition, the kits of the present invention may preferably contain instructions which describe a suitable detection assay. Such kits can be conveniently used, e.g., in clinical settings, to diagnose patients exhibiting symptoms of cancer, in particular patients exhibiting the possible presence of a tumor.

SPECIFIC EMBODIMENTS

I. Identification of Sensitivity and Resistance Genes

The present invention provides genes that are expressed in tumors that are sensitive to a given therapeutic agent and whose expression correlates with sensitivity to that therapeutic agent. The present invention also provides genes that are expressed in tumors that are resistant to a given therapeutic agent and whose expression correlates with resistance to that therapeutic agent. Accordingly, one or more of the sensitivity genes can be used as markers (or surrogate markers) to identify tumors, including tumor cells, that can be successfully treated by that agent. In addition, the markers of the present invention can be used to identify cancers that have become or are at risk of becoming refractory to treatment with the agent. The invention also features marker sets that can predict patients that are likely to respond or not to respond to an agent.

Tables 1-6 show markers whose expression correlates with sensitivity or resistance to a taxane compound and/or a platinum compound. In particular, the Tables set forth markers identified in ovarian tumor samples as sensitive or resistant to the combination therapy of TAXOL and cisplatin. Table 1 sets forth 161 markers indicated as sensitive or resistant to the combination therapy. Table 2A sets forth 19 novel markers also identified as sensitive or resistant to the combination therapy. Table 2B sets forth the nucleotide sequences, SEQ ID NOS:1-19, of the novel markers of Table 2A.

Tables 3A to 6 set forth marker sets that are particularly useful in the methods of the present invention. Specifically, Tables 3A and 3B set forth markers that are predictive of one year clinical outcome, Table 4 sets forth markers that are predictive of four year clinical outcome, and Table 5 sets forth markers that are consistent with CA125 levels. CA125 is a serum marker used to determine a patient's response to chemotherapy. In particular, in ovarian cancer patients, CA125 levels above 35 have been shown to be predictive of reoccurrence while levels below 35 have shown to be predictive of diminished disease. (Skakes, 1995, Cancer, No. 2004). "Clinical outcome" refers to patient status for the given time period, i.e., disease free or recurrence of disease following surgical removal of a tumor. Table 6 sets forth a preferred marker set for ovarian cancer patient response to taxane and platinum chemotherapy, e.g., TAXOL and cisplatin.

II. Determining Sensitivity or Resistance to an Agent

The expression level of the identified sensitivity and resistance genes, or the proteins encoded by the identified sensitivity and resistance genes, may be used to: 1) determine if a tumor can be treated by an agent or combination of agents; 2) determine if a tumor is responding to treatment with an agent or combination of agents; 3) select an appropriate agent or combination of agents for treating a tumor; 4) monitor the effectiveness of an ongoing treatment; and 5) identify new treatments (either single agent or combination of agents). In particular, the identified sensitivity and resistance genes may be utilized as markers (surrogate and/or direct) to determine appropriate therapy, to monitor clinical therapy and human trials of a drug being tested for efficacy, and to develop new agents and therapeutic combinations.

Accordingly, the present invention provides methods for determining whether an agent, e.g., a chemotherapeutic agent, can be used to reduce the growth rate of a tumor comprising the steps of:
 a) obtaining a sample of tumor cells;
 b) determining whether the tumor cells express one or more markers identified in Tables 1-6; and
 c) identifying that an agent is or is not appropriate to treat the tumor based on the expression of one or more markers identified in Tables 1-6.

In another embodiment, the invention provides a method for determining whether an agent can be used to reduce the growth of a tumor, comprising the steps of:

a) obtaining a sample of tumor cells;
b) determining whether the tumor cells express one or more markers identified in Tables 1-6; and
c) identifying that an agent is appropriate to treat the tumor when one or more markers identified in Tables 1-6 are expressed by the tumor cells.

Alternatively, in step (c), an agent can be identified as not being appropriate to treat the tumor when one or more markers identified in Tables 1-6 are not expressed by the tumor cells.

In another embodiment, the invention provides a method for determining whether an agent can be used to reduce the growth of a tumor, comprising the steps of:
a) obtaining a sample of tumor cells;
b) exposing some of the tumor cells to one or more test agents;
c) determining the level of expression of one or more markers identified in Tables 1-6 both in tumor cells exposed to the agent and in tumor cells that have not been exposed to the agent; and
d) identifying that an agent is appropriate to treat the tumor when the expression of the sensitivity markers identified in Tables 1-6 is increased and/or the expression of the resistance markers identified in Tables 1-6 is decreased in the presence of the agent.

Alternatively, in step (d), an agent can be identified as not being appropriate to treat the tumor when the expression of the sensitivity markers identified in Tables 1-6 is decreased and/or the expression of the resistance markers identified in Tables 1-6 is increased in the presence of the agent.

In another embodiment, the invention provides a method for determining whether treatment with an anti-cancer agent should be continued in a cancer patient, comprising the steps of:
a) obtaining two or more samples of tumors cells from a patient at different times during the course of anti-cancer agent treatment;
b) determining the level of expression in the tumors cells of one or more genes which correspond to markers identified in Tables 1-6 in the two or more samples; and
c) continuing the treatment when the expression level of the sensitivity markers identified in Tables 1-6 does not decrease and/or the expression level of the resistance markers identified in Tables 1-6 does not increase during the course of treatment.

Alternatively, in step (c), the treatment is discontinued when the expression level of the sensitivity markers identified in Tables 1-6 is decreased and/or the expression level of the resistance markers identified in Tables 1-6 is increased, during the course of treatment.

The markers of the present invention are predictive of chemotherapeutic agents, generally. In one embodiment of the invention, the agents used in methods of the invention is a taxane compound. In another embodiment, the agent is a platinum compound. In yet another embodiment, the agent is a combination of a taxane compound and a platinum compound e.g., TAXOL and cisplatin, respectively.

In another embodiment of the invention, the expression of genes which correspond to markers identified in Tables 1-6 is detected by measuring mRNA which corresponds to the gene. In yet another embodiment of the invention, the expression of genes which correspond to markers identified in Tables 1-6 is detected by measuring protein which corresponds to the gene. In a further another embodiment of the invention, the tumor cells used in the methods of the invention are obtained from a patient.

In another embodiment, the invention provides a method of treating a patient for cancer by administering to the patient a compound which has been identified as being effective against cancer by methods of the invention described herein.

As used herein, the term "agent" is defined broadly as anything that cancer cells, including tumor cells, may be exposed to in a therapeutic protocol. In the context of the present invention, such agents include, but are not limited to, chemotherapeutic agents, such as anti-metabolic agents, e.g., Ara AC, 5-FU and methotrexate, antimitotic agents, e.g., TAXOL, inblastine and vincristine, alkylating agents, e.g., melphanlan, BCNU and nitrogen mustard, Topoisomerase II inhibitors, e.g., VW-26, topotecan and Bleomycin, strand-breaking agents, e.g., doxorubicin and DHAD, cross-linking agents, e.g., cisplatin and CBDCA, radiation and ultraviolet light. In a preferred embodiment, the agent is a taxane compound (e.g., TAXOL) and/or a platinum compound (e.g., cisplatin).

Further to the above, the language "chemotherapeutic agent" is intended to include chemical reagents which inhibit the growth of proliferating cells or tissues wherein the growth of such cells or tissues is undesirable. Chemotherapeutic agents are well known in the art (see e.g., Gilman A. G., et al., *The Pharmacological Basis of Therapeutics,* 8th Ed., Sec 12: 1202-1263 (1990)), and are typically used to treat neoplastic diseases. The chemotherapeutic agents generally employed in chemotherapy treatments are listed below in Table A.

TABLE A

| CLASS | TYPE OF AGENT | NONPROPRIETARY NAMES (OTHER NAMES) |
|---|---|---|
| Alkylating | Nitrogen Mustards | Mechlorethamine (HN$_2$) |
| | | Cyclophosphamide |
| | | Ifosfamide |
| | | Melphalan (L-sarcolysin) |
| | | Chlorambucil |
| | Ethylenimines And Methylmelamines | Hexamethylmelamine Thiotepa |
| | Alkyl Sulfonates | Busulfan |
| Alkylating | Nitrosoureas | Carmustine (BCNU) |
| | | Lomustine (CCNU) |
| | | Semustine (methyl-CCNU) |
| | | Streptozocin (streptozotocin) |
| | Triazenes | Decarbazine (DTIC; dimethyltriazenoimidazole-carboxamide) |
| | Alkylator | cis-diamminedichloroplatinum II (CDDP) |
| Antimetabolites | Folic Acid Analogs | Methotrexate (amethopterin) |
| | Pyrimidine Analogs | Fluorouracil ('5-fluorouracil; 5-FU) Floxuridine (fluorode-oxyuridine; FUdR) Cytarabine (cytosine arabinoside) |
| | Purine Analogs and Related Inhibitors | Mercaptopuine (6-mercaptopurine; 6-MP) Thioguanine (6-thioguanine; TG) Pentostatin (2'-deoxycoformycin) |
| Natural Products | Vinca Alkaloids | Vinblastin (VLB) Vincristine |
| | Topoisomerase Inhibitors | Etoposide Teniposide Camptothecin |

TABLE A-continued

| CLASS | TYPE OF AGENT | NONPROPRIETARY NAMES (OTHER NAMES) |
|---|---|---|
| | Antibiotics | Topotecan<br>9-amino-campotothecin<br>CPT-11<br>Dactinomycin (actinomycin D)<br>Adriamycin<br>Daunorubicin (daunomycin; rubindomycin)<br>Doxorubicin<br>Bleomycin<br>Plicamycin (mithramycin)<br>Mitomycin (mitomycin C)<br>TAXOL<br>Taxotere |
| | Enzymes | L-Asparaginase |
| | Biological Response Modifiers | Interfon alfa<br>interleukin 2 |
| Miscellaneous Agents | Platinum Coordination Complexes | cis-diamminedichloroplatinum II (CDDP)<br>Carboplatin |
| | Anthracendione | Mitoxantrone |
| | Substituted Urea | Hydroxyurea |
| | Methyl Hydraxzine Derivative | Procarbazine (N-methylhydrazine, (MIH) |
| | Adrenocortical Suppressant | Mitotane (o,p'-DDD)<br>Aminoglutethimide |
| Hormones and Antagonists | Adrenocorticosteroids | Prednisone |
| | Progestins | Hydroxyprogesterone caproate<br>Medroxyprogesterone acetate<br>Megestrol acetate |
| | Estrogens | Diethylstilbestrol<br>Ethinyl estradiol |
| | Antiestrogen | Tamoxifen |
| | Androgens | Testosterone propionate<br>Fluoxymesterone |
| | Antiandrogen | Flutamide |
| | Gonadotropin-releasing Hormone analog | Leuprolide |

The agents tested in the present methods can be a single agent or a combination of agents. For example, the present methods can be used to determine whether a single chemotherapeutic agent, such as methotrexate, can be used to treat a cancer or whether a combination of two or more agents can be used. Preferred combinations will include agents that have different mechanisms of action, e.g., the use of an anti-mitotic agent in combination with an alkylating agent.

As used herein, cancer cells, including tumor cells, refer to cells that divide at an abnormal (increased) rate. Cancer cells include, but are not limited to, carcinomas, such as squamous cell carcinoma, basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; leukemias and lymphomas such as granulocytic leukemia, monocytic leukemia, lymphocytic leukemia, malignant lymphoma, plasmocytoma, reticulum cell sarcoma, or Hodgkins disease; and tumors of the nervous system including glioma, meningoma, medulloblastoma, schwannoma or epidymoma.

The source of the cancer cells used in the present method will be based on how the method of the present invention is being used. For example, if the method is being used to determine whether a patient's cancer can be treated with an agent, or a combination of agents, then the preferred source of cancer cells will be cancer cells obtained from a cancer biopsy from the patient, e.g., a tumor biopsy. Alternatively, a cancer cell line similar to the type of cancer being treated can be assayed. For example if ovarian cancer is being treated, then an ovarian cancer cell line can be used. If the method is being used to monitor the effectiveness of a therapeutic protocol, then a tissue sample from the patient being treated is the preferred source. If the method is being used to identify new therapeutic agents or combinations, any cancer cells, e.g., cells of a cancer cell line, can be used.

A skilled artisan can readily select and obtain the appropriate cancer cells that are used in the present method. For cancer cell lines, sources such as The National Cancer Institute, for the NCI-60 cells, are preferred. For cancer cells obtained from a patient, standard biopsy methods, such as a needle biopsy, can be employed.

Ovarian tumor samples were used to obtain the markers of the present invention. It will thus be appreciated that cells from ovarian tumors are particularly useful in the methods of the present invention.

In the methods of the present invention, the level or amount of expression of one or more genes selected from the group consisting of the genes identified in Tables 1-6 is determined. As used herein, the level or amount of expression refers to the absolute level of expression of an mRNA encoded by the gene or the absolute level of expression of the protein encoded by the gene (i.e., whether or not expression is or is not occurring in the cancer cells).

Generally, it is preferable to determine the expression of two or more of the identified sensitivity or resistance genes, more preferably, three or more of the identified sensitivity or resistance genes, most preferably, a set of the identified sensitivity and/or resistance genes, such as that set forth in Tables 2A and 2B, SEQ ID NOS:1-19. Thus, it is preferable to assess the expression of a panel of sensitivity and resistance genes.

As an alternative to making determinations based on the absolute expression level of selected genes, determinations may be based on the normalized expression levels. Expression levels are normalized by correcting the absolute expression level of a sensitivity or resistance gene by comparing its expression to the expression of a gene that is not a sensitivity or resistance gene, e.g., a housekeeping genes that is constitutively expressed. Suitable genes for normalization include housekeeping genes such as the actin gene. This normalization allows one to compare the expression level in one sample, e.g., a tumor sample, to another sample, e.g., a non-tumor sample, or between samples from different sources.

Alternatively, the expression level can be provided as a relative expression level. To determine a relative expression level of a gene, the level of expression of the gene is determined for 10 or more samples, preferably 50 or more samples, prior to the determination of the expression level for the sample in question. The mean expression level of each of the genes assayed in the larger number of samples is determined and this is used as a baseline expression level for the gene(s)

in question. The expression level of the gene determined for the test sample (absolute level of expression) is then divided by the mean expression value obtained for that gene. This provides a relative expression level and aids in identifying extreme cases of sensitivity or resistance.

Preferably, the samples used will be from similar tumors or from non-cancerous cells of the same tissue origin as the tumor in question. The choice of the cell source is dependent on the use of the relative expression level data. For example, using tumors of similar types for obtaining a mean expression score allows for the identification of extreme cases of sensitivity or resistance. Using expression found in normal tissues as a mean expression score aids in validating whether the sensitivity/resistance gene assayed is tumor specific (versus normal cells). Such a later use is particularly important in identifying whether a sensitivity or resistance gene can serve as a target gene. In addition, as more data is accumulated, the mean expression value can be revised, providing improved relative expression values based on accumulated data.

III. Isolated Nucleic Acid Molecules

One aspect of the invention pertains to isolated nucleic acid molecules that correspond to a marker of the invention, including nucleic acids which encode a polypeptide corresponding to a marker of the invention or a portion of such a polypeptide. Isolated nucleic acids of the invention also include nucleic acid molecules sufficient for use as hybridization probes to identify nucleic acid molecules that correspond to a marker of the invention, including nucleic acids which encode a polypeptide corresponding to a marker of the invention, and fragments of such nucleic acid molecules, e.g., those suitable for use as PCR primers for the amplification or mutation of nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid encoding a protein corresponding to a marker listed in Tables 1-6, can be isolated using standard molecular biology techniques and the sequence information in the database records described herein. Using all or a portion of such nucleic acid sequences, nucleic acid molecules of the invention can be isolated using standard hybridization and cloning techniques (e.g., as described in Sambrook et al., ed., *Molecular Cloning: A Laboratory Manual,* 2nd ed, Cold Spring Harbor Laboratory Press, Cold Spring Harbor, N.Y., 1989).

A nucleic acid molecule of the invention can be amplified using cDNA, mRNA, or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to all or a portion of a nucleic acid molecule of the invention can be prepared by standard synthetic techniques, e.g., using an automated DNA synthesizer.

In another preferred embodiment, an isolated nucleic acid molecule of the invention comprises a nucleic acid molecule which has a nucleotide sequence complementary to the nucleotide sequence of a nucleic acid corresponding to a marker of the invention or to the nucleotide sequence of a nucleic acid encoding a protein which corresponds to a marker of the invention. A nucleic acid molecule which is complementary to a given nucleotide sequence is one which is sufficiently complementary to the given nucleotide sequence that it can hybridize to the given nucleotide sequence thereby forming a stable duplex.

Moreover, a nucleic acid molecule of the invention can comprise only a portion of a nucleic acid sequence, wherein the full length nucleic acid sequence comprises a marker of the invention or which encodes a polypeptide corresponding to a marker of the invention. Such nucleic acids can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a nucleic acid of the invention.

Probes based on the sequence of a nucleic acid molecule of the invention can be used to detect transcripts or genomic sequences corresponding to one or more markers of the invention. The probe comprises a label group attached thereto, e.g., a radioisotope, a fluorescent compound, an enzyme, or an enzyme co-factor. Such probes can be used as part of a diagnostic test kit for identifying cells or tissues which mis-express the protein, such as by measuring levels of a nucleic acid molecule encoding the protein in a sample of cells from a subject, e.g., detecting mRNA levels or determining whether a gene encoding the protein has been mutated or deleted.

The invention further encompasses nucleic acid molecules that differ, due to degeneracy of the genetic code, from the nucleotide sequence of nucleic acids encoding a protein which corresponds to a marker of the invention, and thus encode the same protein.

In addition to the nucleotide sequences described in the database records described herein, it will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

As used herein, the phrase "allelic variant" refers to a nucleotide sequence which occurs at a given locus or to a polypeptide encoded by the nucleotide sequence.

As used herein, the terms "gene" and "recombinant gene" refer to nucleic acid molecules comprising an open reading frame encoding a polypeptide corresponding to a marker of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

In another embodiment, an isolated nucleic acid molecule of the invention is at least 7, 15, 20, 25, 30, 40, 60, 80, 100, 150, 200, 250, 300, 350, 400, 450, 550, 650, 700, 800, 900, 1000, 1200, 1400, 1600, 1800, 2000, 2200, 2400, 2600, 2800, 3000, 3500, 4000, 4500, or more nucleotides in length and hybridizes under stringent conditions to a nucleic acid corresponding to a marker of the invention or to a nucleic acid encoding a protein corresponding to a marker of the invention. As used herein, the term "hybridizes under stringent conditions" is intended to describe conditions for hybridization and washing under which nucleotide sequences at least 75% (80%, 85%, preferably 95%) identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). A preferred, non-limiting example of stringent hybridization conditions for annealing two single-stranded DNA each of which is at least about 100 bases in length and/or for annealing a single-stranded DNA and a single-stranded RNA each of which is at least about 100 bases in length, are hybridization in 6× sodium chloride/sodium citrate (SSC) at about 45° C., followed by one or more washes in 0.2×SSC, 0.1% SDS at 50-65° C. Further preferred hybridization conditions are taught in Lockhart, et al., Nature Biotechnology, Volume 14, 1996 August: 1675-1680; Breslauer, et al., Proc. Natl. Acad. Sci. USA, Volume 83, 1986 June: 3746-3750; Van Ness, et al., Nucleic Acids Research, Volume 19, No. 19, 1991 September: 5143-5151; McGraw, et al., BioTechniques, Volume 8, No. 6 1990: 674-678; and Milner, et al., Nature Biotechnology, Volume 15, 1997 June: 537-541, all expressly incorporated by reference.

In addition to naturally-occurring allelic variants of a nucleic acid molecule of the invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the invention pertains to nucleic acid molecules encoding a polypeptide of the invention that contain changes in amino acid residues that are not essential for activity. Such polypeptides differ in amino acid sequence from the naturally-occurring proteins which correspond to the markers of the invention, yet retain biological activity. In one embodiment, such a protein has an amino acid sequence that is at least about 40% identical, 50%, 60%, 70%, 80%, 90%, 95%, or 98% identical to the amino acid sequence of one of the proteins which correspond to the markers of the invention.

An isolated nucleic acid molecule encoding a variant protein can be created by introducing one or more nucleotide substitutions, additions or deletions into the nucleotide sequence of nucleic acids of the invention, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

The present invention encompasses antisense nucleic acid molecules, i.e., molecules which are complementary to a sense nucleic acid of the invention, e.g., complementary to the coding strand of a double-stranded cDNA molecule corresponding to a marker of the invention or complementary to an mRNA sequence corresponding to a marker of the invention. Accordingly, an antisense nucleic acid of the invention can hydrogen bond to (i.e. anneal with) a sense nucleic acid of the invention. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a polypeptide of the invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a polypeptide corresponding to a selected marker of the invention to thereby inhibit expression of the marker, e.g. by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules of the invention includes direct injection at a tissue site or infusion of the antisense nucleic acid into an ovary-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, *Nucleic Acids Res.* 15:6625-6641). The antisense nucleic acid molecule can also comprise a 2'-o-methylribonucleotide (Inoue et al., 1987, *Nucleic Acids Res.* 15:6131-6148) or a chimeric RNA-DNA analogue (Inoue et al., 1987, *FEBS Lett.* 215:327-330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes as described in Haselhoff and Gerlach, 1988, *Nature* 334:585-591) can be used to catalytically cleave mRNA transcripts to thereby inhibit translation of the protein encoded by the mRNA. A ribozyme having specificity for a nucleic acid molecule encoding a polypeptide corresponding to a marker of the invention can be designed based upon the nucleotide sequence of a cDNA corresponding to the marker. For example, a derivative of a *Tetrahymena* L-19 IVS RNA can be constructed in which the nucleotide sequence of the active site is complementary to the nucleotide sequence to be cleaved (see Cech et al. U.S. Pat. No. 4,987,071; and Cech et al. U.S. Pat. No. 5,116,742). Alternatively, an mRNA encoding a polypeptide of the invention can be used to select a catalytic RNA having a specific ribonuclease activity from a pool of RNA molecules (see, e.g., Bartel and Szostak, 1993, *Science* 261:1411-1418).

The invention also encompasses nucleic acid molecules which form triple helical structures. For example, expression of a polypeptide of the invention can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) *Anticancer Drug Des.* 6(6):569-84; Helene (1992) *Ann. N.Y. Acad. Sci.* 660:27-36; and Maher (1992) *Bioassays* 14(12):807-15.

In various embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al., 1996, *Bioorganic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al (1996), supra; Perry-O'Keefe et al. (1996) *Proc. Natl. Acad. Sci. USA* 93:14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup, 1996, supra; Perry-O'Keefe et al., 1996, *Proc. Natl. Acad. Sci. USA* 93:14670-675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNASE H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) *Nucleic Acids Res.* 24(17):3357-63. For example, a DNA chain can be synthesized on a solid support using standard phosphoramidite coupling chemistry and modified nucleoside analogs. Compounds such as 5'-(4-methoxytrityl) amino-5'-deoxy-thymidine phosphoramidite can be used as a link between the PNA and the 5' end of DNA (Mag et al., 1989, *Nucleic Acids Res.* 17:5973-88). PNA monomers are then coupled in a step-wise manner to produce a chimeric molecule with a 5' PNA segment and a 3' DNA segment (Finn et al., 1996, *Nucleic Acids Res.* 24(17):3357-63). Alternatively, chimeric molecules can be synthesized with a 5' DNA segment and a 3' PNA segment (Peterser et al., 1975, *Bioorganic Med. Chem. Lett.* 5:1119-11124).

In other embodiments, the oligonucleotide can include other appended groups such as peptides (e.g., for targeting host cell receptors in vivo), or agents facilitating transport across the cell membrane (see, e.g., Letsinger et al., 1989, *Proc. Natl. Acad. Sci. USA* 86:6553-6556; Lemaitre et al., 1987, *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, *Bio/Techniques* 6:958-976) or intercalating agents (see, e.g., Zon, 1988, *Pharm. Res.* 5:539-549). To this end, the oligonucleotide can be conjugated to another molecule, e.g., a peptide, hybridization triggered cross-linking agent, transport agent, hybridization-triggered cleavage agent, etc.

The invention also includes molecular beacon nucleic acids having at least one region which is complementary to a nucleic acid of the invention, such that the molecular beacon is useful for quantitating the presence of the nucleic acid of the invention in a sample. A "molecular beacon" nucleic acid is a nucleic acid comprising a pair of complementary regions and having a fluorophore and a fluorescent quencher associated therewith. The fluorophore and quencher are associated with different portions of the nucleic acid in such an orientation that when the complementary regions are annealed with one another, fluorescence of the fluorophore is quenched by the quencher. When the complementary regions of the nucleic acid are not annealed with one another, fluorescence of the fluorophore is quenched to a lesser degree. Molecular beacon nucleic acids are described, for example, in U.S. Pat. No. 5,876,930.

IV. Isolated Proteins and Antibodies

One aspect of the invention pertains to isolated proteins which correspond to individual markers of the invention, and biologically active portions thereof, as well as polypeptide fragments suitable for use as immunogens to raise antibodies directed against a polypeptide corresponding to a marker of the invention. In one embodiment, the native polypeptide corresponding to a marker can be isolated from cells or tissue sources by an appropriate purification scheme using standard protein purification techniques. In another embodiment, polypeptides corresponding to a marker of the invention are produced by recombinant DNA techniques. Alternative to recombinant expression, a polypeptide corresponding to a marker of the invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a polypeptide corresponding to a marker of the invention include polypeptides comprising amino acid sequences sufficiently identical to or derived from the amino acid sequence of the protein corresponding to the marker, which include fewer amino acids than the full length protein, and exhibit at least one activity of the corresponding full-length protein. Typically, biologically active portions comprise a domain or motif with at least one activity of the corresponding protein. A biologically active portion of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the invention.

Preferred polypeptides have the amino acid sequence listed in the one of the GenBank and NUC database records described herein. Other useful proteins are substantially identical (e.g., at least about 40%, preferably 50%, 60%, 70%, 80%, 90%, 95%, or 99%) to one of these sequences and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, (1988) *CABIOS* 4:11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The invention also provides chimeric or fusion proteins corresponding to a marker of the invention. As used herein, a "chimeric protein" or "fusion protein" comprises all or part (preferably a biologically active part) of a polypeptide corresponding to a marker of the invention operably linked to a heterologous polypeptide (i.e., a polypeptide other than the polypeptide corresponding to the marker). Within the fusion protein, the term "operably linked" is intended to indicate that the polypeptide of the invention and the heterologous polypeptide are fused in-frame to each other. The heterologous polypeptide can be fused to the amino-terminus or the carboxyl-terminus of the polypeptide of the invention.

One useful fusion protein is a GST fusion protein in which a polypeptide corresponding to a marker of the invention is fused to the carboxyl terminus of GST sequences. Such fusion proteins can facilitate the purification of a recombinant polypeptide of the invention.

In another embodiment, the fusion protein contains a heterologous signal sequence at its amino terminus. For example, the native signal sequence of a polypeptide corresponding to a marker of the invention can be removed and replaced with a signal sequence from another protein. For example, the gp67 secretory sequence of the baculovirus envelope protein can be used as a heterologous signal sequence (Ausubel et al., ed., *Current Protocols in Molecular Biology*, John Wiley & Sons, NY, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

In yet another embodiment, the fusion protein is an immunoglobulin fusion protein in which all or part of a polypeptide corresponding to a marker of the invention is fused to sequences derived from a member of the immunoglobulin protein family. The immunoglobulin fusion proteins of the invention can be incorporated into pharmaceutical compositions and administered to a subject to inhibit an interaction between a ligand (soluble or membrane-bound) and a protein on the surface of a cell (receptor), to thereby suppress signal transduction in vivo. The immunoglobulin fusion protein can be used to affect the bioavailability of a cognate ligand of a polypeptide of the invention. Inhibition of ligand/receptor interaction can be useful therapeutically, both for treating proliferative and differentiative disorders and for modulating (e.g. promoting or inhibiting) cell survival. Moreover, the immunoglobulin fusion proteins of the invention can be used as immunogens to produce antibodies directed against a polypeptide of the invention in a subject, to purify ligands and in screening assays to identify molecules which inhibit the interaction of receptors with ligands.

Chimeric and fusion proteins of the invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the polypeptide of the invention.

A signal sequence can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to polypeptides from which the signal sequence has been proteolytically cleaved (i.e., the cleavage products). In one embodiment, a nucleic acid sequence encoding a signal sequence can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present invention also pertains to variants of the polypeptides corresponding to individual markers of the invention. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a protein of the invention which function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the invention from a degenerate oligonucleotide sequence. Methods for synthesizing degenerate oligonucleotides are known in the art (see, e.g., Narang, 1983, Tetrahedron 39:3; Itakura et al., 1984, Annu. Rev. Biochem. 53:323; Itakura et al., 1984, Science 198:1056; Ike et al., 1983 Nucleic Acid Res. 11:477).

In addition, libraries of fragments of the coding sequence of a polypeptide corresponding to a marker of the invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan, 1992, Proc. Natl. Acad. Sci. USA 89:7811-7815; Delgrave et al., 1993, Protein Engineering 6(3):327-331).

An isolated polypeptide corresponding to a marker of the invention, or a fragment thereof, can be used as an immunogen to generate antibodies using standard techniques for polyclonal and monoclonal antibody preparation. The full-length polypeptide or protein can be used or, alternatively, the invention provides antigenic peptide fragments for use as immunogens. The antigenic peptide of a protein of the invention comprises at least 8 (preferably 10, 15, 20, or 30 or more) amino acid residues of the amino acid sequence of one of the polypeptides of the invention, and encompasses an epitope of the protein such that an antibody raised against the peptide forms a specific immune complex with a marker of the invention to which the protein corresponds. Preferred epitopes encompassed by the antigenic peptide are regions that are located on the surface of the protein, e.g., hydrophilic regions. Hydrophobicity sequence analysis, hydrophilicity sequence analysis, or similar analyses can be used to identify hydrophilic regions.

An immunogen typically is used to prepare antibodies by immunizing a suitable (i.e. immunocompetent) subject such as a rabbit, goat, mouse, or other mammal or vertebrate. An appropriate immunogenic preparation can contain, for example, recombinantly-expressed or chemically-synthesized polypeptide. The preparation can further include an adjuvant, such as Freund's complete or incomplete adjuvant, or a similar immunostimulatory agent.

Accordingly, another aspect of the invention pertains to antibodies directed against a polypeptide of the invention. The terms "antibody" and "antibody substance" as used interchangeably herein refer to immunoglobulin molecules and immunologically active portions of immunoglobulin molecules, i.e., molecules that contain an antigen binding site which specifically binds an antigen, such as a polypeptide of the invention, e.g., an epitope of a polypeptide of the invention. A molecule which specifically binds to a given polypeptide of the invention is a molecule which binds the polypeptide, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as pepsin. The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope.

Polyclonal antibodies can be prepared as described above by immunizing a suitable subject with a polypeptide of the invention as an immunogen. Preferred polyclonal antibody compositions are ones that have been selected for antibodies directed against a polypeptide or polypeptides of the invention. Particularly preferred polyclonal antibody preparations are ones that contain only antibodies directed against a polypeptide or polypeptides of the invention. Particularly preferred immunogen compositions are those that contain no other human proteins such as, for example, immunogen compositions made using a non-human host cell for recombinant expression of a polypeptide of the invention. In such a manner, the only human epitope or epitopes recognized by the resulting antibody compositions raised against this immunogen will be present as part of a polypeptide or polypeptides of the invention.

The antibody titer in the immunized subject can be monitored over time by standard techniques, such as with an enzyme linked immunosorbent assay (ELISA) using immobilized polypeptide. If desired, the antibody molecules can be harvested or isolated from the subject (e.g., from the blood or serum of the subject) and further purified by well-known techniques, such as protein A chromatography to obtain the IgG fraction. Alternatively, antibodies specific for a protein or polypeptide of the invention can be selected or (e.g., partially purified) or purified by, e.g., affinity chromatography. For example, a recombinantly expressed and purified (or partially purified) protein of the invention is produced as described herein, and covalently or non-covalently coupled to a solid support such as, for example, a chromatography column. The column can then be used to affinity purify antibodies specific for the proteins of the invention from a sample containing antibodies directed against a large number of different epitopes, thereby generating a substantially purified antibody composition, i.e., one that is substantially free of contaminating antibodies. By a substantially purified antibody composition is meant, in this context, that the antibody sample contains at most only 30% (by dry weight) of contaminating antibodies directed against epitopes other than those of the desired protein or polypeptide of the invention, and preferably at most 20%, yet more preferably at most 10%, and most preferably at most 5% (by dry weight) of the sample is contaminating antibodies. A purified antibody composition means that at least 99% of the antibodies in the composition are directed against the desired protein or polypeptide of the invention.

At an appropriate time after immunization, e.g., when the specific antibody titers are highest, antibody-producing cells can be obtained from the subject and used to prepare monoclonal antibodies by standard techniques, such as the hybridoma technique originally described by Kohler and Milstein (1975) *Nature* 256:495-497, the human B cell hybridoma technique (see Kozbor et al., 1983, *Immunol. Today* 4:72), the EBV-hybridoma technique (see Cole et al., pp. 77-96 In *Monoclonal Antibodies and Cancer Therapy*, Alan R. Liss, Inc., 1985) or trioma techniques. The technology for producing hybridomas is well known (see generally *Current Protocols in Immunology*, Coligan et al. ed., John Wiley & Sons, New York, 1994). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against a polypeptide of the invention can be identified and isolated by screening a recombinant combinatorial immunoglobulin library (e.g., an antibody phage display library) with the polypeptide of interest. Kits for generating and screening phage display libraries are commercially available (e.g., the Pharmacia *Recombinant Phage Antibody System*, Catalog No. 27-9400-01; and the Stratagene *SurfZAP Phage Display Kit*, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734.

Additionally, recombinant antibodies, such as chimeric and humanized monoclonal antibodies, comprising both human and non-human portions, which can be made using standard recombinant DNA techniques, are within the scope of the invention. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarily determining regions (CDRs) from the non-human species and a framework region from a human immunoglobulin molecule. (See, e.g., Queen, U.S. Pat. No. 5,585,089, which is incorporated herein by reference in its entirety.) Such chimeric and humanized monoclonal antibodies can be produced by recombinant DNA techniques known in the art, for example using methods described in PCT Publication No. WO 87/02671; European Patent Application 184, 187; European Patent Application 171,496; European Patent Application 173,494; PCT Publication No. WO 86/01533; U.S. Pat. No. 4,816,567; European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559); Morrison (1985) *Science* 229:1202-1207; Oi et al. (1986) *Bio/Techniques* 4:214; U.S. Pat. No. 5,225,539; Jones et al. (1986) *Nature* 321:552-525; Verhoeyan et al. (1988) *Science* 239: 1534; and Beidler et al. (1988) *J. Immunol.* 141:4053-4060.

Antibodies of the invention may be used as therapeutic agents in treating cancers. In a preferred embodiment, completely human antibodies of the invention are used for therapeutic treatment of human cancer patients, particularly those having an ovarian cancer. Such antibodies can be produced, for example, using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide corresponding to a marker of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995) *Int. Rev. Immunol.* 13:65-93). For a detailed discussion of this technology for producing human antibodies and human monoclonal antibodies and protocols for producing such antibodies, see, e.g., U.S. Pat. Nos. 5,625, 126; 5,633,425; 5,661,016; and 5,545,806. In addition, companies such as Abgenix, Inc. (Freemont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a murine antibody, is used to guide the selection of a completely human antibody recognizing the same epitope (Jespers et al., 1994, *Bio/technology* 12:899-903).

An antibody directed against a polypeptide corresponding to a marker of the invention (e.g., a monoclonal antibody) can be used to isolate the polypeptide by standard techniques, such as affinity chromatography or immunoprecipitation. Moreover, such an antibody can be used to detect the marker (e.g., in a cellular lysate or cell supernatant) in order to evaluate the level and pattern of expression of the marker. The antibodies can also be used diagnostically to monitor protein levels in tissues or body fluids (e.g. in an ovary-associated body fluid) as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Further, an antibody (or fragment thereof) can be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha.-interferon, .beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Alternatively, an antibody can be conjugated to a second antibody to form an antibody heteroconjugate as described by Segal in U.S. Pat. No. 4,676,980.

Accordingly, in one aspect, the invention provides substantially purified antibodies or fragments thereof, and non-human antibodies or fragments thereof, which antibodies or fragments specifically bind to a polypeptide comprising an amino acid sequence selected from the group consisting of the amino acid sequences of the present invention, an amino acid sequence encoded by the cDNA of the present invention, a fragment of at least 15 amino acid residues of an amino acid sequence of the present invention, an amino acid sequence which is at least 95% identical to the amino acid sequence of the present invention (wherein the percent identity is determined using the ALIGN program of the GCG software package with a PAM120 weight residue table, a gap length penalty of 12, and a gap penalty of 4) and an amino acid sequence which is encoded by a nucleic acid molecule which hybridizes to a nucleic acid molecule consisting of the nucleic acid molecules of the present invention, or a complement thereof, under conditions of hybridization of 6×SSC at 45° C. and washing in 0.2×SSC, 0.1% SDS at 65° C. In various embodiments, the substantially purified antibodies of the invention, or fragments thereof, can be human, non-human, chimeric and/or humanized antibodies.

In another aspect, the invention provides non-human antibodies or fragments thereof, which antibodies or fragments specifically bind to a polypeptide comprising an amino acid sequence selected from the group consisting of: the amino acid sequence of the present invention, an amino acid sequence encoded by the cDNA of the present invention, a fragment of at least 15 amino acid residues of the amino acid sequence of the present invention, an amino acid sequence which is at least 95% identical to the amino acid sequence of the present invention (wherein the percent identity is determined using the ALIGN program of the GCG software package with a PAM120 weight residue table, a gap length penalty of 12, and a gap penalty of 4) and an amino acid sequence which is encoded by a nucleic acid molecule which hybridizes to a nucleic acid molecule consisting of the nucleic acid molecules of the present invention, or a complement thereof, under conditions of hybridization of 6×SSC at 45° C. and washing in 0.2×SSC, 0.1% SDS at 65° C. Such non-human antibodies can be goat, mouse, sheep, horse, chicken, rabbit, or rat antibodies. Alternatively, the non-human antibodies of the invention can be chimeric and/or humanized antibodies. In addition, the non-human antibodies of the invention can be polyclonal antibodies or monoclonal antibodies.

In still a further aspect, the invention provides monoclonal antibodies or fragments thereof, which antibodies or fragments specifically bind to a polypeptide comprising an amino acid sequence selected from the group consisting of the amino acid sequences of the present invention, an amino acid sequence encoded by the cDNA of the present invention, a fragment of at least 15 amino acid residues of an amino acid sequence of the present invention, an amino acid sequence which is at least 95% identical to an amino acid sequence of the present invention (wherein the percent identity is determined using the ALIGN program of the GCG software package with a PAM120 weight residue table, a gap length penalty of 12, and a gap penalty of 4) and an amino acid sequence which is encoded by a nucleic acid molecule which hybridizes to a nucleic acid molecule consisting of the nucleic acid molecules of the present invention, or a complement thereof, under conditions of hybridization of 6×SSC at 45° C. and washing in 0.2×SSC, 0.1% SDS at 65° C. The monoclonal antibodies can be human, humanized, chimeric and/or non-human antibodies.

The substantially purified antibodies or fragments thereof may specifically bind to a signal peptide, a secreted sequence, an extracellular domain, a transmembrane or a cytoplasmic domain or cytoplasmic membrane of a polypeptide of the invention. In a particularly preferred embodiment, the substantially purified antibodies or fragments thereof, the non-human antibodies or fragments thereof, and/or the monoclonal antibodies or fragments thereof, of the invention specifically bind to a secreted sequence or an extracellular domain of the amino acid sequences of the present invention.

Any of the antibodies of the invention can be conjugated to a therapeutic moiety or to a detectable substance. Non-limiting examples of detectable substances that can be conjugated to the antibodies of the invention are an enzyme, a prosthetic group, a fluorescent material, a luminescent material, a bioluminescent material, and a radioactive material.

The invention also provides a kit containing an antibody of the invention conjugated to a detectable substance, and instructions for use. Still another aspect of the invention is a pharmaceutical composition comprising an antibody of the invention and a pharmaceutically acceptable carrier. In preferred embodiments, the pharmaceutical composition contains an antibody of the invention, a therapeutic moiety, and a pharmaceutically acceptable carrier.

Still another aspect of the invention is a method of making an antibody that specifically recognizes a polypeptide of the present invention, the method comprising immunizing a mammal with a polypeptide. The polypeptide used as an immungen comprises an amino acid sequence selected from the group consisting of the amino acid sequence of the present invention, an amino acid sequence encoded by the cDNA of the nucleic acid molecules of the present invention, a fragment of at least 15 amino acid residues of the amino acid sequence of the present invention, an amino acid sequence which is at least 95% identical to the amino acid sequence of the present invention (wherein the percent identity is determined using the ALIGN program of the GCG software package with a PAM120 weight residue table, a gap length penalty of 12, and a gap penalty of 4) and an amino acid sequence which is encoded by a nucleic acid molecule which hybridizes to a nucleic acid molecule consisting of the nucleic acid molecules of the present invention, or a complement thereof, under conditions of hybridization of 6×SSC at 45° C. and washing in 0.2×SSC, 0.1% SDS at 65° C.

After immunization, a sample is collected from the mammal that contains an antibody that specifically recognizes the polypeptide. Preferably, the polypeptide is recombinantly produced using a non-human host cell. Optionally, the antibodies can be further purified from the sample using techniques well known to those of skill in the art. The method can further comprise producing a monoclonal antibody-producing cell from the cells of the mammal. Optionally, antibodies are collected from the antibody-producing cell.

V. Recombinant Expression Vectors and Host Cells

Another aspect of the invention pertains to vectors, preferably expression vectors, containing a nucleic acid encoding a polypeptide corresponding to a marker of the invention (or a portion of such a polypeptide). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequencers) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Methods in Enzymology: Gene Expression Technology* vol. 185, Academic Press, San Diego, Calif. (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein.

The recombinant expression vectors of the invention can be designed for expression of a polypeptide corresponding to a marker of the invention in prokaryotic (e.g., *E. coli*) or eukaryotic cells (e.g., insect cells fusing baculovirus expression vectors), yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., 1988, *Gene* 69:301-315) and pET 11d (Studier et al., p. 60-89, In *Gene Expression Technology: Methods in Enzymology* vol. 185, Academic Press, San Diego, Calif., 1991). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, p. 119-128, In *Gene Expression Technology: Methods in Enzymology* vol. 185, Academic Press, San Diego, Calif., 1990. Another strategy is to alter the nucleic acid sequence of the nucleic acid to be inserted into an expression vector so that the individual codons for each amino acid are those preferentially utilized in *E. coli* (Wada et al., 1992, *Nucleic Acids Res.* 20:2111-2118). Such alteration of nucleic acid sequences of the invention can be carried out by standard DNA synthesis techniques.

In another embodiment, the expression vector is a yeast expression vector. Examples of vectors for expression in yeast *S. cerevisiae* include pYepSec1 (Baldari et al., 1987, *EMBO J.* 6:229-234), pMFa (Kurjan and Herskowitz, 1982, *Cell* 30:933-943), pJRY88 (Schultz et al., 1987, *Gene* 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al., 1983, *Mol. Cell. Biol.* 3:2156-2165) and the pVL series (Lucklow and Summers, 1989, Virology 170:31-39).

In yet another embodiment, a nucleic acid of the invention is expressed in mammalian cells using a mammalian expression vector. Examples of mammalian expression vectors include pCDM8 (Seed, 1987, *Nature* 329:840) and pMT2PC (Kaufman et al., 1987, *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, *Genes Dev.* 1:268-277), lymphoid-specific promoters (Calame and Eaton, 1988, *Adv. Immunol.* 43:235-275), in particular promoters of T cell receptors (Winoto and Baltimore, 1989, *EMBO J.* 8:729-733) and immunoglobulins (Banerji et al., 1983, *Cell* 33:729-740; Queen and Baltimore, 1983, *Cell* 33:741-748), neuron-specific promoters (e.g., the neurofilament promoter; Byrne and Ruddle, 1989, *Proc. Natl. Acad. Sci. USA* 86:5473-5477), pancreas-specific promoters (Edlund et al., 1985, *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990, *Science* 249:374-379) and the α-fetoprotein promoter (Camper and Tilghman, 1989, *Genes Dev.* 3:537-546).

The invention further provides a recombinant expression vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al., 1986, *Trends in Genetics*, Vol. 1(1).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce a polypeptide corresponding to a marker of the invention. Accordingly, the invention further provides methods for producing a polypeptide corresponding to a marker of the invention using the host cells of the invention. In one embodiment, the method comprises culturing the host cell of invention (into which a recombinant expression vector encoding a polypeptide of the invention has been introduced) in a suitable medium such that the marker is produced. In another embodiment, the method further comprises isolating the marker polypeptide from the medium or the host cell.

The host cells of the invention can also be used to produce nonhuman transgenic animals. For example, in one embodiment, a host cell of the invention is a fertilized oocyte or an embryonic stem cell into which a sequences encoding a polypeptide corresponding to a marker of the invention have been introduced. Such host cells can then be used to create non-human transgenic animals in which exogenous sequences encoding a marker protein of the invention have been introduced into their genome or homologous recombinant animals in which endogenous gene(s) encoding a polypeptide corresponding to a marker of the invention sequences have been altered. Such animals are useful for studying the function and/or activity of the polypeptide corresponding to the marker and for identifying and/or evaluating modulators of polypeptide activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a nucleic acid encoding a polypeptide corresponding to a marker of the invention into the male pronuclei of a fertilized oocyte, e.g., by microinjection, retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to the transgene to direct expression of the polypeptide of the invention to particular cells. Methods for generating transgenic animals via embryo manipulation and microinjection, particularly animals such as mice, have become conventional in the art and are described, for example, in U.S. Pat. Nos. 4,736,866 and 4,870,009, 4,873,191 and in Hogan, *Manipulating the Mouse Embryo*, Cold Spring Harbor Laboratory Press, Cold Spring Harbor, N.Y., 1986. Similar methods are used for production of other transgenic animals. A transgenic founder animal can be identified based upon the presence of the transgene in its genome and/or expression of mRNA encoding the transgene in tissues or cells of the animals. A transgenic founder animal can then be used to breed additional animals carrying the transgene. Moreover, transgenic animals carrying the transgene can further be bred to other transgenic animals carrying other transgenes.

To create an homologous recombinant animal, a vector is prepared which contains at least a portion of a gene encoding a polypeptide corresponding to a marker of the invention into which a deletion, addition or substitution has been introduced to thereby alter, e.g., functionally disrupt, the gene. In a preferred embodiment, the vector is designed such that, upon homologous recombination, the endogenous gene is functionally disrupted (i.e., no longer encodes a functional protein; also referred to as a "knock out" vector). Alternatively, the vector can be designed such that, upon homologous recombination, the endogenous gene is mutated or otherwise altered but still encodes functional protein (e.g., the upstream regulatory region can be altered to thereby alter the expression of the endogenous protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid sequences are of sufficient length for successful homologous recombination with the endogenous gene. Typically, several kilobases of flanking DNA (both at the 5' and 3' ends) are included in the vector (see, e.g., Thomas and Capecchi, 1987, *Cell* 51:503 for a description of homologous recombination vectors). The vector is introduced into an embryonic stem cell line (e.g., by electroporation) and cells in which the introduced gene has homologously recombined with the endogenous gene are selected (see, e.g., Li et al., 1992, *Cell* 69:915). The selected cells are then injected into a blastocyst of an animal (e.g., a mouse) to form aggregation chimeras (see, e.g., Bradley, *Teratocarcinomas and Embryonic Stem Cells: A Practical Approach*, Robertson, Ed., IRL, Oxford, 1987, pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823-829 and in PCT Publication NOS. WO 90/11354, WO 91/01140, WO 92/0968, and WO 93/04169.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al., 1991, *Science* 251:1351-1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810-813 and PCT Publication NOS. WO 97/07668 and WO 97/07669.

VI. Pharmaceutical Compositions

The nucleic acid molecules, polypeptides, and antibodies (also referred to herein as "active compounds") corresponding to a marker of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a polypeptide or nucleic acid corresponding to a marker of the invention. Such methods comprise formulating a pharmaceutically acceptable carrier with an agent which modulates expression or activity of a polypeptide or nucleic acid corresponding to a marker of the invention. Such compositions can further include additional active agents. Thus, the invention further includes methods for preparing a pharmaceutical composition by formulating a pharmaceutically acceptable carrier with an agent which modulates expression or activity of a polypeptide or nucleic acid corresponding to a marker of the invention and one or more additional active compounds.

The invention also provides methods (also referred to herein as "screening assays") for identifying modulators, i.e., candidate or test compounds or agents (e.g., peptides, peptidomimetics, peptoids, small molecules or other drugs) which (a) bind to the marker, or (b) have a modulatory (e.g., stimulatory or inhibitory) effect on the activity of the marker or, more specifically, (c) have a modulatory effect on the interactions of the marker with one or more of its natural substrates (e.g., peptide, protein, hormone, co-factor, or nucleic acid), or (d) have a modulatory effect on the expression of the marker. Such assays typically comprise a reaction between the marker and one or more assay components. The other components may be either the test compound itself, or a combination of test compound and a natural binding partner of the marker.

The test compounds of the present invention may be obtained from any available source, including systematic libraries of natural and/or synthetic compounds. Test compounds may also be obtained by any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al., 1994, *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, Anticancer Drug Des. 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J Med. Chem.* 37:2678; Cho et al. (1993) *Science* 261:1303; Carrell et al. (1994) *Angew. Chem. Int. Ed Engl.* 33:2059; Carell et al. (1994) *Angew. Chem. Int. Ed Engl.* 33:2061; and in Gallop et al. (1994) *J. Med. Chem.* 37:1233.

Libraries of compounds may be presented in solution (e.g., Houghten, 1992, *Biotechniques* 13:412-421), or on beads (Lam, 1991, *Nature* 354:82-84), chips (Fodor, 1993, *Nature* 364:555-556), bacteria and/or spores, (Ladner, U.S. Pat. No. 5,223,409), plasmids (Cull et al, 1992, *Proc Natl Acad Sci USA* 89:1865-1869) or on phage (Scott and Smith, 1990, *Science* 249:386-390; Devlin, 1990, *Science* 249:404-406; Cwirla et al, 1990, *Proc. Natl. Acad. Sci.* 87:6378-6382; Felici, 1991, *J. Mol. Biol.* 222:301-310; Ladner, supra.).

In one embodiment, the invention provides assays for screening candidate or test compounds which are substrates of a marker or biologically active portion thereof. In another embodiment, the invention provides assays for screening candidate or test compounds which bind to a marker or biologically active portion thereof. Determining the ability of the test compound to directly bind to a marker can be accomplished, for example, by coupling the compound with a radioisotope or enzymatic label such that binding of the compound to the marker can be determined by detecting the labeled marker compound in a complex. For example, compounds (e.g., marker substrates) can be labeled with $^{125}I$, $^{35}S$, $^{14}C$, or $^{3}H$, either directly or indirectly, and the radioisotope detected by direct counting of radioemission or by scintillation counting. Alternatively, assay components can be enzymatically labeled with, for example, horseradish peroxidase, alkaline phosphatase, or luciferase, and the enzymatic label detected by determination of conversion of an appropriate substrate to product.

In another embodiment, the invention provides assays for screening candidate or test compounds which modulate the activity of a marker or a biologically active portion thereof. In all likelihood, the marker can, in vivo, interact with one or more molecules, such as but not limited to, peptides, proteins, hormones, cofactors and nucleic acids. For the purposes of this discussion, such cellular and extracellular molecules are referred to herein as "binding partners" or marker "substrate".

One necessary embodiment of the invention in order to facilitate such screening is the use of the marker to identify its natural in vivo binding partners. There are many ways to accomplish this which are known to one skilled in the art. One example is the use of the marker protein as "bait protein" in a two-hybrid assay or three-hybrid assay (see, e.g., U.S. Pat. No. 5,283,317; Zervos et al, 1993, *Cell* 72:223-232; Madura et al, 1993, *J. Biol. Chem.* 268:12046-12054; Bartel et al, 1993, *Biotechniques* 14:920-924; Iwabuchi et al, 1993 *Oncogene* 8:1693-1696; Brent WO94/10300) in order to identify other proteins which bind to or interact with the marker (binding partners) and, therefore, are possibly involved in the natural function of the marker. Such marker binding partners are also likely to be involved in the propagation of signals by the marker or downstream elements of a marker-mediated signaling pathway. Alternatively, such marker binding partners may also be found to be inhibitors of the marker.

The two-hybrid system is based on the modular nature of most transcription factors, which consist of separable DNA-binding and activation domains. Briefly, the assay utilizes two different DNA constructs. In one construct, the gene that encodes a marker protein fused to a gene encoding the DNA binding domain of a known transcription factor (e.g., GAL- 4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a marker-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be readily detected and cell colonies containing the functional transcription factor can be isolated and used to obtain the cloned gene which encodes the protein which interacts with the marker protein.

In a further embodiment, assays may be devised through the use of the invention for the purpose of identifying compounds which modulate (e.g., affect either positively or negatively) interactions between a marker and its substrates and/or binding partners. Such compounds can include, but are not limited to, molecules such as antibodies, peptides, hormones, oligonucleotides, nucleic acids, and analogs thereof. Such compounds may also be obtained from any available source, including systematic libraries of natural and/or synthetic compounds. The preferred assay components for use in this embodiment is an ovarian cancer marker identified herein, the known binding partner and/or substrate of same, and the test compound. Test compounds can be supplied from any source.

The basic principle of the assay systems used to identify compounds that interfere with the interaction between the marker and its binding partner involves preparing a reaction mixture containing the marker and its binding partner under conditions and for a time sufficient to allow the two products to interact and bind, thus forming a complex. In order to test an agent for inhibitory activity, the reaction mixture is prepared in the presence and absence of the test compound. The test compound can be initially included in the reaction mixture, or can be added at a time subsequent to the addition of the marker and its binding partner. Control reaction mixtures are incubated without the test compound or with a placebo. The formation of any complexes between the marker and its binding partner is then detected. The formation of a complex in the control reaction, but less or no such formation in the reaction mixture containing the test compound, indicates that the compound interferes with the interaction of the marker and its binding partner. Conversely, the formation of more complex in the presence of compound than in the control reaction indicates that the compound may enhance interaction of the marker and its binding partner.

The assay for compounds that interfere with the interaction of the marker with its binding partner may be conducted in a heterogeneous or homogeneous format. Heterogeneous assays involve anchoring either the marker or its binding partner onto a solid phase and detecting complexes anchored to the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the markers and the binding partners (e.g., by competition) can be identified by conducting the reaction in the presence of the test substance, i.e., by adding the test substance to the reaction mixture prior to or simultaneously with the marker and its interactive binding partner. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the marker or its binding partner is anchored onto a solid surface or matrix, while the other corresponding non-anchored component may be labeled, either directly or indirectly. In practice, microtitre plates are often utilized for this approach. The anchored species can be immobilized by a number of methods, either non-covalent or covalent, that are typically well known to one who practices the art. Non-covalent attachment can often be accomplished simply by coating the solid surface with a solution of the marker or its binding partner and drying. Alternatively, an immobilized antibody specific for the assay component to be anchored can be used for this purpose. Such surfaces can often be prepared in advance and stored.

In related embodiments, a fusion protein can be provided which adds a domain that allows one or both of the assay components to be anchored to a matrix. For example, glutathione-S-transferase/marker fusion proteins or glutathione-S-transferase/binding partner can be adsorbed onto glutathione sepharose beads (Sigma Chemical, St. Louis, Mo.) or glutathione derivatized microtiter plates, which are then combined with the test compound or the test compound and either the non-adsorbed marker or its binding partner, and the mixture incubated under conditions conducive to complex formation (e.g., physiological conditions). Following incubation, the beads or microtiter plate wells are washed to remove any unbound assay components, the immobilized complex assessed either directly or indirectly, for example, as described above. Alternatively, the complexes can be dissociated from the matrix, and the level of marker binding or activity determined using standard techniques.

Other techniques for immobilizing proteins on matrices can also be used in the screening assays of the invention. For example, either a marker or a marker binding partner can be immobilized utilizing conjugation of biotin and streptavidin. Biotinylated marker protein or target molecules can be prepared from biotin-NHS (N-hydroxy-succinimide) using techniques known in the art (e.g. biotinylation kit, Pierce Chemicals, Rockford, Ill.), and immobilized in the wells of streptavidin-coated 96 well plates (Pierce Chemical). In certain embodiments, the protein-immobilized surfaces can be prepared in advance and stored.

In order to conduct the assay, the corresponding partner of the immobilized assay component is exposed to the coated surface with or without the test compound. After the reaction is complete, unreacted assay components are removed (e.g., by washing) and any complexes formed will remain immobilized on the solid surface. The detection of complexes anchored on the solid surface can be accomplished in a number of ways. Where the non-immobilized component is pre-labeled, the detection of label immobilized on the surface indicates that complexes were formed. Where the non-immobilized component is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds which modulate (inhibit or enhance) complex formation or which disrupt preformed complexes can be detected.

In an alternate embodiment of the invention, a homogeneous assay may be used. This is typically a reaction, analogous to those mentioned above, which is conducted in a liquid phase in the presence or absence of the test compound. The formed complexes are then separated from unreacted components, and the amount of complex formed is determined. As mentioned for heterogeneous assay systems, the order of addition of reactants to the liquid phase can yield information about which test compounds modulate (inhibit or enhance) complex formation and which disrupt preformed complexes.

In such a homogeneous assay, the reaction products may be separated from unreacted assay components by any of a number of standard techniques, including but not limited to: differential centrifugation, chromatography, electrophoresis and immunoprecipitation. In differential centrifugation, complexes of molecules may be separated from uncomplexed molecules through a series of centrifugal steps, due to the different sedimentation equilibria of complexes based on their different sizes and densities (see, for example, Rivas, G., and Minton, A. P., *Trends Biochem Sci* 1993 August; 18(8): 284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the complex as compared to the uncomplexed molecules may be exploited to differentially separate the complex from the remaining individual reactants, for example through the use of ion-exchange chromatography resins. Such resins and chromatographic techniques are well known to one skilled in the art (see, e.g., Heegaard, 1998, *J. Mol. Recognit.* 11: 141-148; Hage and Tweed, 1997, *J. Chromatogr. B. Biomed Sci. Appl.,* 699:499-525). Gel electrophoresis may also be employed to separate complexed molecules from unbound species (see, e.g., Ausubel et al (eds.), In: Current Protocols in Molecular Biology, J. Wiley & Sons, New York. 1999). In this technique, protein or nucleic acid complexes are separated based on size or charge, for example. In order to maintain the binding interaction during the electrophoretic process, nondenaturing gels in the absence of reducing agent are typically preferred, but conditions appropriate to the particular interactants will be well known to one skilled in the art. Immunoprecipitation is another common technique utilized for the isolation of a protein-protein complex from solution (see, e.g., Ausubel et al (eds.), In: Current Protocols in Molecular Biology, J. Wiley & Sons, New York. 1999). In this technique, all proteins binding to an antibody specific to one of the binding molecules are precipitated from solution by conjugating the antibody to a polymer bead that may be readily collected by centrifugation. The bound assay components are released from the beads (through a specific proteolysis event or other technique well known in the art which will not disturb the protein-protein interaction in the complex), and a second immunoprecipitation step is performed, this time utilizing antibodies specific for the correspondingly different interacting assay component. In this manner, only formed complexes should remain attached to the beads. Variations in complex formation in both the presence and the absence of a test compound can be compared, thus offering information about the ability of the compound to modulate interactions between the marker and its binding partner.

Also within the scope of the present invention are methods for direct detection of interactions between the marker and its natural binding partner and/or a test compound in a homogeneous or heterogeneous assay system without further sample manipulation. For example, the technique of fluorescence energy transfer may be utilized (see, e.g., Lakowicz et al, U.S. Pat. No. 5,631,169; Stavrianopoulos et al, U.S. Pat. No. 4,868,103). Generally, this technique involves the addition of a fluorophore label on a first 'donor' molecule (e.g., marker or test compound) such that its emitted fluorescent energy will be absorbed by a fluorescent label on a second, 'acceptor' molecule (e.g., marker or test compound), which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter). A test substance which either enhances or hinders participation of one of the species in the preformed complex will result in the generation of a signal variant to that of background. In this way, test substances that modulate interactions between a marker and its binding partner can be identified in controlled assays.

In another embodiment, modulators of marker expression are identified in a method wherein a cell is contacted with a candidate compound and the expression of mRNA or protein, corresponding to a marker in the cell, is determined. The level of expression of mRNA or protein in the presence of the candidate compound is compared to the level of expression of mRNA or protein in the absence of the candidate compound. The candidate compound can then be identified as a modulator of marker expression based on this comparison. For example, when expression of marker mRNA or protein is greater (statistically significantly greater) in the presence of the candidate compound than in its absence, the candidate compound is identified as a stimulator of marker mRNA or protein expression. Conversely, when expression of marker mRNA or protein is less (statistically significantly less) in the presence of the candidate compound than in its absence, the candidate compound is identified as an inhibitor of marker mRNA or protein expression. The level of marker mRNA or protein expression in the cells can be determined by methods described herein for detecting marker mRNA or protein.

In another aspect, the invention pertains to a combination of two or more of the assays described herein. For example, a modulating agent can be identified using a cell-based or a cell free assay, and the ability of the agent to modulate the activity of a marker protein can be further confirmed in vivo, e.g., in a whole animal model for cellular transformation and/or tumorigenesis.

This invention further pertains to novel agents identified by the above-described screening assays. Accordingly, it is within the scope of this invention to further use an agent identified as described herein in an appropriate animal model. For example, an agent identified as described herein (e.g., an marker modulating agent, an antisense marker nucleic acid molecule, an marker-specific antibody, or an marker-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

It is understood that appropriate doses of small molecule agents and protein or polypeptide agents depends upon a number of factors within the knowledge of the ordinarily skilled physician, veterinarian, or researcher. The dose(s) of these agents will vary, for example, depending upon the identity, size, and condition of the subject or sample being treated, further depending upon the route by which the composition is to be administered, if applicable, and the effect which the practitioner desires the agent to have upon the nucleic acid or polypeptide of the invention. Exemplary doses of a small molecule include milligram or microgram amounts per kilogram of subject or sample weight (e.g. about 1 microgram per kilogram to about 500 milligrams per kilogram, about 100 micrograms per kilogram to about 5 milligrams per kilogram, or about 1 microgram per kilogram to about 50 micrograms per kilogram). Exemplary doses of a protein or polypeptide include gram, milligram or microgram amounts per kilogram of subject or sample weight (e.g. about 1 microgram per kilogram to about 5 grams per kilogram, about 100 micrograms per kilogram to about 500 milligrams per kilogram, or about 1 milligram per kilogram to about 50 milligrams per kilogram). It is furthermore understood that appropriate doses of one of these agents depend upon the potency of the agent with respect to the expression or activity to be modulated. Such appropriate doses can be determined using the assays described herein. When one or more of these agents is to be administered to an animal (e.g. a human) in order to modulate expression or activity of a polypeptide or nucleic acid of the invention, a physician, veterinarian, or researcher can, for example, prescribe a relatively low dose at first, subsequently increasing the dose until an appropriate response is obtained. In addition, it is understood that the specific dose level for any particular animal subject will depend upon a variety of factors including the activity of the specific agent employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediamine-tetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium, and then incorporating the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches, and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes having monoclonal antibodies incorporated therein or thereon) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the ovarian epithelium). A method for lipidation of antibodies is described by Cruikshank et al. (1997) *J. Acquired Immune Deficiency Syndromes and Human Retrovirology* 14:193.

The nucleic acid molecules corresponding to a marker of the invention can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al., 1994, *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

VII. Monitoring the Effectiveness of an Anti-Cancer Agent

As discussed above, the identified sensitivity and resistance genes can also be used as markers to assess whether a tumor has become refractory to an ongoing treatment (e.g., a chemotherapeutic treatment). When a tumor is no longer responding to a treatment the expression profile of the tumor cells will change: the level of expression of one or more of the sensitivity genes will be reduced and/or the level of expression of one or more of the resistance genes will increase.

In such a use, the invention provides methods for determining whether an anti-cancer treatment should be continued in a cancer patient, comprising the steps of:

a) obtaining two or more samples of cancer cells from a patient undergoing anti-cancer therapy;

b) determining the level of expression of one or more markers selected from the group consisting of the markers of Tables 1-6 in the sample exposed to the agent and in a sample of cancer cells that is not exposed to the agent; and c) discontinuing or altering treatment when the expression of one or more sensitivity genes decreases and/or when the expression of one or more resistance genes increases.

As used herein, a patient refers to any subject undergoing treatment for cancer. The preferred subject will be a human patient undergoing chemotherapy treatment.

This embodiment of the present invention relies on comparing two or more samples obtained from a patient undergoing anti-cancer treatment. In general, it is preferable to obtain a first sample from the patient prior to beginning therapy and one or more samples during treatment. In such a use, a baseline of expression prior to therapy is determined and then changes in the baseline state of expression is monitored during the course of therapy. Alternatively, two or more successive samples obtained during treatment can be used without the need of a pre-treatment baseline sample. In such a use, the first sample obtained from the subject is used as a baseline for determining whether the expression of a particular gene is increasing or decreasing.

In general, when monitoring the effectiveness of a therapeutic treatment, two or more samples from the patient are examined. Preferably, three or more successively obtained samples are used, including at least one pretreatment sample.

VIII. Detection Assays

An exemplary method for detecting the presence or absence of a polypeptide or nucleic acid corresponding to a marker of the invention in a biological sample involves obtaining a biological sample (e.g. an ovarian tumor sample) from a test subject and contacting the biological sample with a compound or an agent capable of detecting the polypeptide or nucleic acid (e.g., mRNA, genomic DNA, or cDNA). The detection methods of the invention can thus be used to detect mRNA, protein, cDNA, or genomic DNA, for example, in a biological sample in vitro as well as in vivo. For example, in vitro techniques for detection of mRNA include Northern hybridizations and in situ hybridizations. In vitro techniques for detection of a polypeptide corresponding to a marker of the invention include enzyme linked immunosorbent assays (ELISAs), Western blots, immunoprecipitations and immunofluorescence. In vitro techniques for detection of genomic DNA include Southern hybridizations. Furthermore, in vivo techniques for detection of a polypeptide corresponding to a marker of the invention include introducing into a subject a labeled antibody directed against the polypeptide. For example, the antibody can be labeled with a radioactive marker whose presence and location in a subject can be detected by standard imaging techniques.

A general principle of such diagnostic and prognostic assays involves preparing a sample or reaction mixture that may contain a marker, and a probe, under appropriate conditions and for a time sufficient to allow the marker and probe to interact and bind, thus forming a complex that can be removed and/or detected in the reaction mixture. These assays can be conducted in a variety of ways.

For example, one method to conduct such an assay would involve anchoring the marker or probe onto a solid phase support, also referred to as a substrate, and detecting target marker/probe complexes anchored on the solid phase at the end of the reaction. In one embodiment of such a method, a sample from a subject, which is to be assayed for presence and/or concentration of marker, can be anchored onto a carrier or solid phase support. In another embodiment, the reverse situation is possible, in which the probe can be anchored to a solid phase and a sample from a subject can be allowed to react as an unanchored component of the assay.

There are many established methods for anchoring assay components to a solid phase. These include, without limitation, marker or probe molecules which are immobilized through conjugation of biotin and streptavidin. Such biotinylated assay components can be prepared from biotin-NHS(N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the marker or probe belongs. Well-known supports or carriers include, but are not limited to, glass, polystyrene, nylon, polypropylene, nylon, polyethylene, dextran, amylases, natural and modified celluloses, polyacrylamides, gabbros, and magnetite.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of marker/probe complexes anchored to the solid phase can be accomplished in a number of methods outlined herein.

In a preferred embodiment, the probe, when it is the unanchored assay component, can be labeled for the purpose of detection and readout of the assay, either directly or indirectly, with detectable labels discussed herein and which are well-known to one skilled in the art.

It is also possible to directly detect marker/probe complex formation without further manipulation or labeling of either component (marker or probe), for example by utilizing the technique of fluorescence energy transfer (see, for example, Lakowicz et al., U.S. Pat. No. 5,631,169; Stavrianopoulos, et al., U.S. Pat. No. 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determination of the ability of a probe to recognize a marker can be accomplished without labeling either assay component (probe or marker) by utilizing a technology such as real-time Biomolecular Interaction Analysis (BIA) (see, e.g., Sjolander, S, and Urbaniczky, C., 1991, *Anal. Chem.* 63:2338-2345 and Szabo et al., 1995, *Curr. Opin. Struct. Biol.* 5:699-705). As used herein, "BIA" or "surface plasmon resonance" is a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with marker and probe as solutes in a liquid phase. In such an assay, the complexed marker and probe are separated from uncomplexed components by any of a number of standard techniques, including but not limited to: differential centrifugation, chromatography, electrophoresis and immunoprecipitation. In differential centrifugation, marker/probe complexes may be separated from uncomplexed assay components through a series of centrifugal steps, due to the different sedimentation equilibria of complexes based on their different sizes and densities (see, for example, Rivas, G., and Minton, A. P., 1993, *Trends Biochem Sci.* 18(8):284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the marker/probe complex as compared to the uncomplexed components may be exploited to differentiate the complex from uncomplexed components, for example through the utilization of ion-exchange chromatography resins. Such resins and chromatographic techniques are well known to one skilled in the art (see, e.g., Heegaard, N. H., 1998, *J. Mol. Recognit.* Winter 11(1-6):141-8; Hage, D. S., and Tweed, S. A. *J Chromatogr B Biomed Sci Appl* 1997 Oct. 10; 699(1-2):499-525). Gel electrophoresis may also be employed to separate complexed assay components from unbound components (see, e.g., Ausubel et al., ed., *Current Protocols in Molecular Biology*, John Wiley & Sons, New York, 1987-1999). In this technique, protein or nucleic acid complexes are separated based on size or charge, for example. In order to maintain the binding interaction during the electrophoretic process, non-denaturing gel matrix materials and conditions in the absence of reducing agent are typically preferred. Appropriate conditions to the particular assay and components thereof will be well known to one skilled in the art.

In a particular embodiment, the level of mRNA corresponding to the marker can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from ovarian cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding a marker of the present invention. Other suitable probes for use in the diagnostic assays of the invention are described herein. Hybridization of an mRNA with the probe indicates that the marker in question is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the markers of the present invention.

An alternative method for determining the level of mRNA corresponding to a marker of the present invention in a sample involves the process of nucleic acid amplification, e.g., by rtPCR (the experimental embodiment set forth in Mullis, 1987, U.S. Pat. No. 4,683,202), ligase chain reaction (Barany, 1991, *Proc. Natl. Acad. Sci. USA*, 88:189-193), self sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the ovarian cells prior to detection. In such methods, a cell or tissue sample is prepared/processed using known histological methods. The sample is then immobilized on a support, typically a glass slide, and then contacted with a probe that can hybridize to mRNA that encodes the marker.

As an alternative to making determinations based on the absolute expression level of the marker, determinations may be based on the normalized expression level of the marker. Expression levels are normalized by correcting the absolute expression level of a marker by comparing its expression to the expression of a gene that is not a marker, e.g., a housekeeping gene that is constitutively expressed. Suitable genes for normalization include housekeeping genes such as the actin gene, or epithelial cell-specific genes. This normalization allows the comparison of the expression level in one sample, e.g., a patient sample, to another sample, e.g., a non-ovarian cancer sample, or between samples from different sources.

Alternatively, the expression level can be provided as a relative expression level. To determine a relative expression level of a marker, the level of expression of the marker is determined for 10 or more samples of normal versus cancer cell isolates, preferably 50 or more samples, prior to the determination of the expression level for the sample in question. The mean expression level of each of the genes assayed in the larger number of samples is determined and this is used as a baseline expression level for the marker. The expression level of the marker determined for the test sample (absolute level of expression) is then divided by the mean expression value obtained for that marker. This provides a relative expression level.

In another embodiment of the present invention, a polypeptide corresponding to a marker is detected. A preferred agent for detecting a polypeptide of the invention is an antibody capable of binding to a polypeptide corresponding to a marker of the invention, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

A variety of formats can be employed to determine whether a sample contains a protein that binds to a given antibody. Examples of such formats include, but are not limited to, enzyme immunoassay (EIA), radioimmunoassay (RIA), Western blot analysis and enzyme linked immunoabsorbant assay (ELISA). A skilled artisan can readily adapt known protein/antibody detection methods for use in determining whether ovarian cells express a marker of the present invention.

In one format, antibodies, or antibody fragments, can be used in methods such as Western blots or immunofluorescence techniques to detect the expressed proteins. In such uses, it is generally preferable to immobilize either the antibody or proteins on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present invention. For example, protein isolated from ovarian cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

The invention also encompasses kits for detecting the presence of a polypeptide or nucleic acid corresponding to a marker of the invention in a biological sample (e.g. an ovary-associated body fluid such as a urine sample). Such kits can be used to determine if a subject is suffering from or is at increased risk of developing ovarian cancer. For example, the kit can comprise a labeled compound or agent capable of detecting a polypeptide or an mRNA encoding a polypeptide corresponding to a marker of the invention in a biological sample and means for determining the amount of the polypeptide or mRNA in the sample (e.g., an antibody which binds the polypeptide or an oligonucleotide probe which binds to DNA or mRNA encoding the polypeptide). Kits can also include instructions for interpreting the results obtained using the kit.

For antibody-based kits, the kit can comprise, for example: (1) a first antibody (e.g., attached to a solid support) which binds to a polypeptide corresponding to a marker of the invention; and, optionally, (2) a second, different antibody which binds to either the polypeptide or the first antibody and is conjugated to a detectable label.

For oligonucleotide-based kits, the kit can comprise, for example: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also comprise, e.g., a buffering agent, a preservative, or a protein stabilizing agent. The kit can further comprise components necessary for detecting the detectable label (e.g., an enzyme or a substrate). The kit can also contain a control sample or a series of control samples which can be assayed and compared to the test sample. Each component of the kit can be enclosed within an individual container and all of the various containers can be within a single package, along with instructions for interpreting the results of the assays performed using the kit.

IX. Electronic Apparatus Readable Media and Arrays

Electronic apparatus readable media comprising a marker of the present invention is also provided. As used herein, "electronic apparatus readable media" refers to any suitable medium for storing, holding or containing data or information that can be read and accessed directly by an electronic apparatus. Such media can include, but are not limited to: magnetic storage media, such as floppy discs, hard disc storage medium, and magnetic tape; optical storage media such as compact disc; electronic storage media such as RAM, ROM, EPROM, EEPROM and the like; general hard disks and hybrids of these categories such as magnetic/optical storage media. The medium is adapted or configured for having recorded thereon a marker of the present invention.

As used herein, the term "electronic apparatus" is intended to include any suitable computing or processing apparatus or other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the markers of the present invention.

A variety of software programs and formats can be used to store the marker information of the present invention on the electronic apparatus readable medium. For example, the nucleic acid sequence corresponding to the markers can be represented in a word processing text file, formatted in commercially-available software such as WordPerfect and MicroSoft Word, or represented in the form of an ASCII file, stored in a database application, such as DB2, Sybase, Oracle, or the like, as well as in other forms. Any number of dataprocessor structuring formats (e.g., text file or database) may be employed in order to obtain or create a medium having recorded thereon the markers of the present invention.

By providing the markers of the invention in readable form, one can routinely access the marker sequence information for a variety of purposes. For example, one skilled in the art can use the nucleotide or amino acid sequences of the present invention in readable form to compare a target sequence or target structural motif with the sequence information stored within the data storage means. Search means are used to identify fragments or regions of the sequences of the invention which match a particular target sequence or target motif.

The invention also includes an array comprising a marker of the present invention. The array can be used to assay expression of one or more genes in the array. In one embodiment, the array can be used to assay gene expression in a tissue to ascertain tissue specificity of genes in the array. In this manner, up to about 36,000 genes can be simultaneously assayed for expression. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array.

The array is also useful for ascertaining the effect of the expression of a gene on the expression of other genes in the same cell or in different cells. This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes that could serve as a molecular target for diagnosis or therapeutic intervention.

SPECIFIC EXAMPLES

A. Identification of Sensitivity and Resistant Markers

Tumors from 58 ovarian cancer patients were used in this study. In particular, RNA was isolated from ovarian tumors using a Quagen RNeasy kit according to the manufacturers directions. Probes for transcriptional profiling were generated by reverse transcribing the RNA into cDNA with Superscript II Reverse transcriptase, done in the presence of $x^{33}$P-dCTP. Transcriptional profiling was then performed using the radio labeled cDNA probe by hybridizing the probe to nylon filter arrays on which were spotted >36,000 target cDNAs. The hybridbizing of the specific cDNA probes to the target cDNAs was done for 18 hours at 65° C. in the presence of Cot1 and Salmon sperm DNA to block non-specific binding. The filters were then washed once with 4% SDS-low stringency wash buffer and twice with 1% SDS-high stringency wash buffer. After drying the filters they were placed on a Fuji phospho-imager screen for 48 hours. The image was then read on a Fuji phosphoimager, the intensity of the cDNA probe bound to target cDNA digitized using Grid Guru and AIMZOO software packages.

The response of the 58 ovarian cancer patients was determined by analyzing clinical oncologist reports. One year outcome was used to define those patients that had no evidence of disease (NED) for the twelve months following the final round of the first chemotherapy. NED was determined by either a second-look surgery or by increasing levels of the serum marker, CA125 (see, supra). Four year outcome was used to define those patients who either had NED for four years post-chemotherapy or patients who died of ovarian cancer within three years post-chemotherapy. CA125 levels were measured during the six months post-chemotherapy. Patients who attain CA125 levels>35 have relapsed while those with CA125 levels<35 generally show NED.

Candidate markers that are likely to predict the outcome of cancer patients to a combined TAXOL/cisplatin therapy were selected by using a combination of predictive algorithms. Statistical algorithms were then used to identify the markers of the present invention.

B. Therapeutic Agents

The markers of the present invention are shown to be sensitive or resistant to TAXOL. TAXOL is a chemical compound within a family of taxane compounds which are art-recognized as being a family of related compounds. The language "taxane compound" is intended to include TAXOL, compounds which are structurally similar to TAXOL and/or analogs of TAXOL. The language "taxane compound" can also include "mimics". "Mimics" is intended to include compounds which may not be structurally similar to TAXOL but mimic the therapeutic activity of TAXOL or structurally similar taxane compounds in vivo. The taxane compounds of this invention are those compounds which are useful for inhibiting tumor growth in subjects (patients). The term taxane compound also is intended to include pharmaceutically acceptable salts of the compounds. Taxane compounds have previously been described in U.S. Pat. Nos. 5,641,803, 5,665,671, 5,380,751, 5,728,687, 5,415,869, 5,407,683, 5,399,363, 5,424,073, 5,157,049, 5,773,464, 5,821,263, 5,840,929, 4,814,470, 5,438,072, 5,403,858, 4,960,790, 5,433,364, 4,942,184, 5,362,831, 5,705,503, and 5,278,324, all of which are expressly incorporated by reference.

The structure of TAXOL, shown below, offers many groups capable of being synthetically functionalized to alter the physical or pharmaceutical properties of TAXOL.

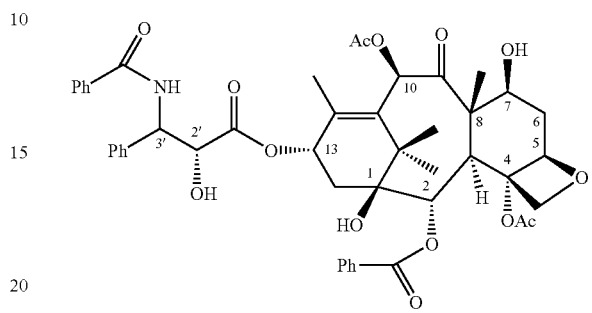

For example, a well known semi-synthetic analog of TAXOL, named Taxotere (docetaxel), has also been found to have good anti-tumor activity in animal models. Taxotere has t-butoxy amide at the 3' position and a hydroxyl group at the C10 position (U.S. Pat. No. 5,840,929).

Other examples of TAXOL derivatives include those mentioned in U.S. Pat. No. 5,840,929 which are directed to derivatives of TAXOL having the formula:

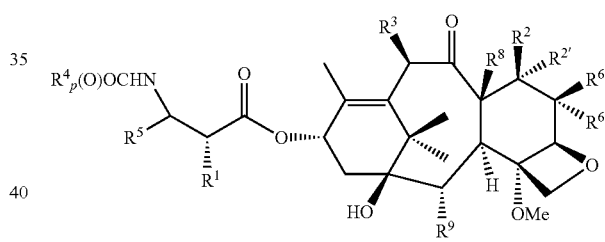

wherein $R^1$ is hydroxy, —OC(O)$R^x$, or —OC(O)O$R^x$; $R^2$ is hydrogen, hydroxy, —OC(O)$R^x$, or —OC(O)O$R^x$; $R^{2'}$ is hydrogen, hydroxy, or fluoro; $R^{6'}$ is hydrogen or hydroxy or $R^{2'}$ and $R^{6'}$ can together form an oxirane ring; $R^3$ is hydrogen, $C_{1-6}$ alkyloxy, hydroxy, —OC(O)$R^x$, —OC(O)O$R^x$, —OCONR$^7$R$^{11}$; $R^8$ is methyl or $R^8$ and $R^2$ together can form a cyclopropane ring; $R^6$ is hydrogen or $R^6$ and $R^2$ can together form a bond; $R^9$ is hydroxy or —OC(O)$R^x$; $R^7$ and $R^{11}$ are independently $C_{1-6}$ alkyl, hydrogen, aryl, or substituted aryl; $R^4$ and $R^5$ are independently $C_{1-6}$ alkyl, $C_{2-6}$ alkenyl, $C_{2-6}$ alkynyl, or —Z—$R^{10}$; Z is a direct bond, $C_{1-6}$ alkyl, or $C_{2-6}$ alkenyl; $R^{10}$ is aryl, substituted aryl, $C_{3-6}$ cycloalkyl, $C_{2-6}$ alkenyl, $C_{1-6}$ alkyl, all can be optionally substituted with one to six same or different halogen atoms or hydroxy; $R^x$ is a radical of the formula:

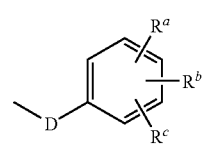

wherein D is a bond or $C_{1-6}$ alkyl; and $R^a$, $R^b$ and $R^c$ are independently hydrogen, amino, $C_{1-6}$ alkyl or $C_{1-6}$ alkoxy.

Further examples of $R^x$ include methyl, hydroxymethyl, ethyl, n-propyl, isopropyl, n-butyl, isobutyl, chloromethyl, 2,2,2-trichloroethyl, cyclopropyl, cyclobutyl, cyclopentyl, cyclohexyl, ethenyl, 2-propenyl, phenyl, benzyl, bromophenyl, 4-aminophenyl, 4-methylaminophenyl, 4-methylphenyl, 4-methoxyphenyl and the like. Examples of $R^4$ and $R^5$ include 2-propenyl, isobutenyl, 3-furanyl (3-furyl), 3-thienyl, phenyl, naphthyl, 4-hydroxyphenyl, 4-methoxyphenyl, 4-fluorophenyl, 4-trifluoromethylphenyl, methyl, ethyl, n-propyl, isopropyl, n-butyl, isobutyl, t-butyl, ethenyl, 2-propenyl, 2-propynyl, benzyl, phenethyl, phenylethenyl, 3,4-dimethoxyphenyl, 2-furanyl (2-furyl), 2-thienyl, 2-(2-furanyl)ethenyl, 2-methylpropyl, cyclopropyl, cyclobutyl, cyclopentyl, cyclohexyl, cyclohexylmethyl, cyclohexylethyl and the like.

TAXOL derivatives can be readily made by following the well established paclitaxel chemistry. For example, C2, C6, C7, C10, and/or C8 position can be derivatized by essentially following the published procedure, into a compound in which $R^3$, $R^8$, $R^2$, $R^{2'}$, $R^9$, $R^{6'}$ and $R^6$ have the meanings defined earlier. Subsequently, C4-acetyloxy group can be converted to the methoxy group by a sequence of steps. For example, for converting C2-benzoyloxy to other groups see, S. H. Chen et al, *Bioorganic and Medicinal Chemistry Letters*, Vol. 4, No. 3, pp 479-482 (1994); for modifying C10-acetyloxy see, J. Kant et al, *Tetrahedron Letters*, Vol. 35, No. 31, pp 5543-5546 (1994) and U.S. Pat. No. 5,294,637 issued Mar. 15, 1994; for making C10 and/or C7 unsubstituted (deoxy) derivatives see, European Patent Application 590 267A2 published Apr. 6, 1994 and PCT application WO 93/06093 published Apr. 1, 1993; for making 7β,8β-methano, 6,7-α,α-dihydroxy and 6,7-olefinic groups see, R. A. Johnson, *Tetrahedron Letters*, Vol. 35, No 43, pp 7893-7896 (1994), U.S. Pat. No. 5,254,580, issued Oct. 19, 1993, and European Patent Application 600 517A1 published Jun. 8, 1994; for making C7/C6 oxirane see, U.S. Pat. No. 5,395,850 issued Mar. 7, 1995; for making C7-epi-fluoro see, G. Roth et al, *Tetrahedron Letters*, Vol 36, pp 1609-1612 (1993); for forming C7 esters and carbonates see, U.S. Pat. No. 5,272,171 issued Dec. 21, 1993 and S. H. Chen et al., *Tetrahedron*, 49, No. 14, pp 2805-2828 (1993).

In U.S. Pat. No. 5,773,464, TAXOL derivatives containing epoxides at the $C_{10}$ position are disclosed as antitumor agents. Other C-10 taxane analogs have also appeared in the literature. Taxanes with alkyl substituents at C-10 have been reported in a published PCT patent application WO 9533740. The synthesis of C-10 epi hydroxy or acyloxy compounds is disclosed in PCT application WO 96/03394. Additional C-10 analogs have been reported in Tetrahedron Letters 1995, 36(12), 1985-1988; *J. Org. Chem.* 1994, 59, 4015-4018 and references therein; K. V. Rao et. al. *Journal of Medicinal Chemistry* 1995, 38 (17), 3411-3414; J. Kant et. al. *Tetrahedron Lett.* 1994, 35(31), 5543-5546; WO 9533736; WO 93/02067; U.S. Pat. No. 5,248,796; WO 9415929; and WO 94/15599.

Other relevant TAXOL derivatives include the sulfenamide taxane derivatives described in U.S. Pat. No. 5,821,263. These compounds are characterized by the C3' nitrogen bearing one or two sulfur substiuents. These compounds have been useful in the treatment of cancers such as ovarian, breast, lung, gastic, colon, head, neck, melanoma, and leukemia.

U.S. Pat. No. 4,814,470 discusses TAXOL derivatives with hydroxyl or acetyl group at the C10 position and hydroxy or t-butylcarbonyl at C2' and C3' positions.

U.S. Pat. No. 5,438,072 discusses TAXOL derivatives with hydroxyl or acetate groups at the $C_{10}$ position and a C2' substitutent of either t-butylcarbonyl or benzoylamino.

U.S. Pat. No. 4,960,790 discusses derivatives of TAXOL which have, at the C2' and/or C7 position a hydrogen, or the residue of an amino acid selected from the group consisting of alanine, leucine, isoleucine, saline, phenylalanine, proline, lysine, and arginine, or a group of the formula:

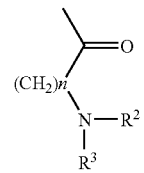

wherein n is an integer of 1 to 3 and $R^2$ and $R^3$ are each hydrogen on an alkyl radical having one to three carbon atoms or wherein $R^2$ and $R^3$ together with the nitrogen atom to which they are attached form a saturated heterocyclic ring having four to five carbon atoms, with the proviso that at least one of the substituents are not hydrogen.

Other similar water soluble TAXOL derivatives are discussed in U.S. Pat. Nos. 4,942,184, 5,433,364, and in U.S. Pat. No. 5,278,324.

Many TAXOL derivatives may also include protecting groups such as, for example, hydroxy protecting groups. "Hydroxy protecting groups" include, but are not limited to, ethers such as methyl, t-butyl, benzyl, p-methoxybenzyl, p-nitrobenzyl, allyl, trityl, methoxymethyl, methoxyethoxymethyl, ethoxyethyl, tetrahydropyranyl, tetrahydrothiopyranyl, dialkylsilylethers, such as dimethylsilyl ether, and trialkylsilyl ethers such as trimethylsilyl ether, triethylsilyl ether, and t-butyldimethylsilyl ether, esters such as benzoyl, acetyl, phenylacetyl, formyl, mono-, di-, and trihaloacetyl such as chloroacetyl, dichloroacetyl, trichloroacetyl, trifluoroacetyl; and carbonates such as methyl, ethyl, 2,2,2-trichloroethyl, allyl, benzyl, and p-nitrophenyl. Additional examples of hydroxy protecting groups may be found in standard reference works such as Greene and Wuts, *Protective Groups in Organic Synthesis*, 2d Ed., 1991, John Wiley & Sons, and McOmie; and *Protective Groups in Organic Chemistry*, 1975, Plenum Press. Methods for introducing and removing protecting groups are also found in such textbooks.

The markers of the present invention are also shown to be sensitive to cis-Diamminedichloroplatinum (II), otherwise known as cisplatin. Cisplatin is a chemical compound within a family of platinum coordination complexes which are art-recognized as being a family of related compounds. Cisplatin was the first platinum compound shown to have anti-malignant properties. The language "platinum compounds" is intended to include cisplatin, compounds which are structurally similar to cisplatin, as well as analogs and derivatives of cisplatin. The language "platinum compounds" can also include "mimics". "Mimics" is intended to include compounds which may not be structurally similar to cisplatin but mimic the therapeutic activity of cisplatin or structurally related compounds in vivo.

The platinum compounds of this invention are those compounds which are useful for inhibiting tumor growth in subjects (patients). More than 1000 platinum-containing compounds have been synthesized and tested for therapeutic properties. One of these, carboplatin, has been approved for treatment of ovarian cancer. Both cisplatin and carboplatin are amenable to intravenous delivery. However, compounds of the invention can be formulated for therapeutic delivery by any number of strategies. The term platinum compounds also is intended to include pharmaceutically acceptable salts and related compounds. Platinum compounds have previously been described in U.S. Pat. Nos. 6,001,817, 5,945,122, 5,942,389, 5,922,689, 5,902,610, 5,866,617, 5,849,790, 5,824,346, 5,616,613, and 5,578,571, all of which are expressly incorporated by reference.

Cisplatin and related compounds are thought to enter cells through diffusion, whereupon the molecule likely undergos metabolic processing to yield the active metabolite of the drug, which then reacts with nucleic acids and proteins. Cisplatin has biochemical properties similar to that of bifunctional alkylating agents, producing interstrand, intrastrand, and monofunctional adduct cross-linking with DNA.

C. Sensitivity Assays and Identification of Therapeutic and Drug Screening Targets A sample of cancerous cells with unknown sensitivity to a given therapeutic agent is obtained from a patient. An expression level is measured in the sample for a gene corresponding to one of the markers identified in Tables 1-6. If the gene is expressed, and the marker of the invention to which the gene corresponds is a sensitivity marker, then the therapeutic agent will be effective against the cancer. Accordingly, if a sensitivity marker is not expressed, then the therapeutic agent will not be effective against the cancer. If a resistance marker of the invention is expressed, then the therapeutic agent will not be effective against the cancer. Accordingly, if the resistance marker is not expressed, then the therapeutic agent will be effective against the cancer. Thus, by examining the expression of one or more of the identified markers in a sample of cancer cells, it is possible to determine which therapeutic agent(s), or combination of agents, to use as the appropriate treatment agents.

By examining the expression of one or more of the identified markers in a sample of cancer cells taken from a patient during the course of therapeutic treatment, it is also possible to determine whether the therapeutic agent is continuing to work or whether the cancer has become resistant (refractory) to the treatment protocol. For example, a cancer patient receiving a treatment of TAXOL would have cancer cells removed and monitored for the expression of a marker. If the expression level of a sensitivity marker remains substantially the same, the treatment with TAXOL would continue. However, a significant decrease in sensitivity marker expression or increased expression of a resistance marker, would suggest that the cancer may have become resistant to TAXOL and another chemotherapy protocol should be initiated to treat the patient.

Importantly, these determinations can be made on a patient by patient basis or on an agent by agent (or combinations of agents). Thus, one can determine whether or not a particular therapeutic treatment is likely to benefit a particular patient or group/class of patients, or whether a particular treatment should be continued.

The identified markers further provide previously unknown or unrecognized targets for the development of anti-cancer agents, such as chemotherapeutic compounds, and can be used as targets in developing single agent treatment as well as combinations of agents for the treatment of cancer.

Summary of the Data Provided in the Tables

The following terms are used throughout the Tables:

"Image Clone ID" corresponds to the cDNA clone number from the IMAGE Consortium (see, for example Lennon, G., et al., 1996, *Genomics* 33:151-152; and http://www-bio.lln-l.gov/bbrp/image/image.html). All referenced IMAGE clone sequences are expressly incorporated herein by reference.

"Accession No." corresponds to the GenBank accession number assigned the particular sequence (see, for example http://www.ncbi.nlm.nih.gov/Entrez/nucleotide.html). All referenced GenBank sequences are expressly incorporated herein by reference.

"Nuc Seq Id" corresponds to the GenBank GI number (see supra).

"Cluster Id" corresponds to the NCBI Unigene Cluster number.

"Cluster Title" refers to the name of the NCBI Unigene Cluster.

"Gene" refers to the common name of the sequence.

"Sensitivity or Resistance" refers to whether a gene is a sensitivity or resistance marker.

"Clone" refers to an assigned reference number for each sequence listed.

"Annotation" refers to a brief description of the sequence.

Other Embodiments

The present invention is not to be limited in scope by the specific embodiments described that are intended as single illustrations of individual aspects of the invention and functionally equivalent methods and components are within the scope of the invention, in addition to those shown and described herein will become apparent to those skilled in the art from the foregoing description and accompanying drawings. Such modifications are intended to fall within the scope of the appended claims.

All references cited herein, including journal articles, patents, and databases are expressly incorporated by reference.

TABLE 1

| Image Clone ID | Accession No. | Nuc Seq Id | Cluster Id | Cluster Title | Gene | Sensitivity or Resistance |
|---|---|---|---|---|---|---|
| 26617 | R39862 | g797478 | Hs.10247 | activated leucocyte cell adhesion molecule | ALCAM | Resistance |
| 26617 | R13558 | g766634 | Hs.10247 | activated leucocyte cell adhesion molecule | ALCAM | Resistance |
| 27544 | R40057 | g822754 | Hs.112360 | prominin (mouse)-like 1 | PROML1 | Sensitivity |
| 32567 | R43511 | g821440 | Hs.34853 | inhibitor of DNA binding 4, dominant negative helix-loop-helix protein | ID4 | Sensitivity |
| 32567 | R20393 | g775027 | Hs.34853 | inhibitor of DNA binding 4, dominant negative helix-loop-helix protein | ID4 | Sensitivity |
| 33267 | R43855 | g821734 | Hs.162 | insulin-like growth factor binding protein 2 (36 kD) | IGFBP2 | Resistance |

TABLE 1-continued

| Image Clone ID | Accession No. | Nuc Seq Id | Cluster Id | Cluster Title | Gene | Sensitivity or Resistance |
|---|---|---|---|---|---|---|
| 51221 | H19246 | g885486 | Hs.106635 | ortholog of rat pippin | PIPPIN | Sensitivity |
| 51221 | H19245 | g885485 | Hs.106635 | ortholog of rat pippin | PIPPIN | Sensitivity |
| 66317 | T66816 | g676256 | Hs.7644 | H1 histone family, member 2 | H1F2 | Sensitivity |
| 66317 | T66815 | g676255 | Hs.7644 | H1 histone family, member 2 | H1F2 | Sensitivity |
| 66420 | R16069 | g767878 | Hs.189713 | ESTs | — | Sensitivity |
| 66498 | R16030 | g768012 | Hs.21688 | ESTs | — | Resistance |
| 66498 | R16130 | g767939 | Hs.21688 | ESTs | — | Resistance |
| 121661 | T97616 | g746961 | Hs.226410 | ESTs | — | Sensitivity |
| 122906 | T99784 | g749521 | Hs.186545 | ESTs | — | Sensitivity |
| 127192 | R08260 | g760183 | Hs.20131 | ESTs | — | Sensitivity |
| 128126 | R09561 | g761484 | Hs.1369 | decay accelerating factor for complement (CD55, Cromer blood group system) | DAF | Resistance |
| 128126 | R09672 | g761595 | Hs.1369 | decay accelerating factor for complement (CD55, Cromer blood group system) | DAF | Resistance |
| 153505 | R48303 | g810329 | Hs.80552 | dermatopontin | DPT | Resistance |
| 153505 | R48405 | g810431 | Hs.80552 | dermatopontin | DPT | Resistance |
| 154172 | R52030 | g813932 | Hs.111732 | IgG Fc binding protein | FC(GAMMA)BP | Sensitivity |
| 154654 | R55185 | g824480 | Hs.3321 | ESTs, Highly similar to IROQUOIS-CLASS HOMEODOMAIN PROTEIN IRX-3 [*M. musculus*] | — | Sensitivity |
| 159455 | H15746 | g880566 | Hs.74573 | similar to vaccinia virus HindIII K4L ORF | HU-K4 | Resistance |
| 159455 | H15747 | g880567 | Hs.74573 | similar to vaccinia virus HindIII K4L ORF | HU-K4 | Resistance |
| 199243 | R95869 | g981529 | Hs.35467 | EST | — | Sensitivity |
| 203348 | H54285 | g994432 | Hs.9829 | ESTs | — | Sensitivity |
| 234907 | H73080 | g1046466 | Hs.82007 | KIAA0094 protein | KIAA0094 | Resistance |
| 234907 | H73079 | g1046465 | Hs.82007 | KIAA0094 protein | KIAA0094 | Resistance |
| 242642 | H94977 | g1102610 | Hs.42041 | EST | — | Sensitivity |
| 243741 | N49629 | g1190795 | Hs.44532 | diubiquitin | UBD | Sensitivity |
| 243741 | N33920 | g1154320 | Hs.44532 | diubiquitin | UBD | Sensitivity |
| 245330 | N76677 | g1239255 | Hs.251664 | insulin-like growth factor 2 (somatomedin A) | IGF2 | Resistance |
| 245330 | N54596 | g1195916 | Hs.251664 | insulin-like growth factor 2 (somatomedin A) | IGF2 | Resistance |
| 261828 | H99196 | g1123864 | Hs.226216 | ESTs | — | Sensitivity |
| 261828 | N24479 | g1138629 | Hs.226216 | ESTs | — | Sensitivity |
| 274677 | R84629 | g943035 | Hs.169338 | ESTs | — | Resistance |
| 274677 | R85394 | g943800 | Hs.169338 | ESTs | — | Resistance |
| 277173 | N44209 | g1182737 | Hs.181357 | laminin receptor 1 (67 kD, ribosomal protein SA) | LAMR1 | Sensitivity |
| 277173 | N34316 | g1155458 | Hs.181357 | laminin receptor 1 (67 kD, ribosomal protein SA) | LAMR1 | Sensitivity |
| 284220 | N53534 | g1194700 | Hs.171763 | CD22 antigen | CD22 | Resistance |
| 291880 | N67487 | g1219612 | Hs.83551 | microfibrillar-associated protein 2 | MFAP2 | Resistance |
| 291880 | W03413 | g1275326 | Hs.83551 | microfibrillar-associated protein 2 | MFAP2 | Resistance |
| 295723 | N66925 | g1219050 | Hs.49275 | ESTs | — | Sensitivity |
| 298417 | N74131 | g1231416 | Hs.82961 | trefoil factor 3 (intestinal) | TFF3 | Sensitivity |
| 322443 | W39215 | g1320924 | Hs.238927 | *Homo sapiens* mRNA; cDNA DKFZp434H1235 (from clone DKFZp434H1235); partial cds | — | Sensitivity |
| 322443 | W16424 | g1289598 | Hs.238927 | *Homo sapiens* mRNA; cDNA DKFZp434H1235 (from clone DKFZp434H1235); partial cds | — | Sensitivity |
| 322723 | W15465 | g1289894 | Hs.93231 | ESTs | — | Sensitivity |
| 322723 | W39618 | g1321460 | Hs.93231 | ESTs | — | Sensitivity |
| 324699 | W47134 | g1331784 | Hs.184019 | *Homo sapiens* clone 23551 mRNA sequence | — | Sensitivity |
| 324699 | W47096 | g1331890 | Hs.184019 | *Homo sapiens* clone 23551 mRNA sequence | — | Sensitivity |
| 344942 | W72861 | g1383016 | Hs.109299 | protein tyrosine phosphatase, receptor type, f polypeptide (PTPRF), interacting protein (liprin), alpha 3 | PPFIA3 | Sensitivity |
| 344942 | W75957 | g1386331 | Hs.109299 | protein tyrosine phosphatase, receptor type, f polypeptide (PTPRF), interacting protein (liprin), alpha 3 | PPFIA3 | Sensitivity |
| 344958 | W72892 | g1383027 | Hs.214507 | ESTs | — | Sensitivity |
| 344958 | W76097 | g1386341 | Hs.214507 | ESTs | — | Sensitivity |
| 377799 | AA777001 | g2836332 | Hs.79378 | cyclin A1 | CCNA1 | Resistance |
| 430077 | AA010003 | g1471050 | Hs.79103 | aminolevulinate, delta-, synthase 2 (sideroblastic/hypochromic anemia) | ALAS2 | Sensitivity |
| 430077 | AA010004 | g1471051 | Hs.79103 | aminolevulinate, delta-, synthase 2 (sideroblastic/hypochromic anemia) | ALAS2 | Sensitivity |
| 431944 | AA678160 | g2658682 | Hs.117106 | ESTs | — | Resistance |

TABLE 1-continued

| Image Clone ID | Accession No. | Nuc Seq Id | Cluster Id | Cluster Title | Gene | Sensitivity or Resistance |
|---|---|---|---|---|---|---|
| 436348 | AA776448 | g2835782 | Hs.122614 | ESTs, Weakly similar to apoptotic protease activating factor 1 [*M. musculus*] | — | Sensitivity |
| 436782 | AA702821 | g2705934 | Hs.124778 | ESTs | — | Sensitivity |
| 451706 | AA707650 | g2717568 | Hs.267289 | polymerase (DNA directed), alpha | POLA | Sensitivity |
| 460487 | AA677706 | g2658228 | Hs.347 | lactotransferrin | LTF | Sensitivity |
| 461468 | AA705029 | g2714947 | Hs.163036 | ESTs | — | Resistance |
| 488945 | AA047077 | g1524975 | Hs.75733 | amylase, alpha 2B; pancreatic | AMY2B | Sensitivity |
| 488945 | AA047078 | g1524976 | Hs.180149 | ESTs, Highly similar to ALPHA-AMYLASE 2B PRECURSOR [*H. sapiens*] | — | Sensitivity |
| 489637 | AA099445 | g1645393 | Hs.181060 | apelin; peptide ligand for APJ receptor | APELIN | Sensitivity |
| 489637 | AA101878 | g1645281 | Hs.181060 | apelin; peptide ligand for APJ receptor | APELIN | Sensitivity |
| 490600 | AA101616 | g1648684 | Hs.155210 | FOS-like antigen 2 | FOSL2 | Resistance |
| 490600 | AA101617 | g1648685 | Hs.155210 | FOS-like antigen 2 | FOSL2 | Resistance |
| 506516 | AA708619 | g2718537 | Hs.128856 | CSR1 protein | CSR1 | Resistance |
| 506583 | AA708512 | g2718430 | Hs.25537 | cardiotrophin 1 | CTF1 | Resistance |
| 510576 | AA055768 | g1548168 | Hs.25615 | YDD19 protein | YDD19 | Sensitivity |
| 510576 | AA055880 | g1548218 | Hs.91011 | anterior gradient 2 (*Xenepus laevis*) homolog | AGR2 | Sensitivity |
| 592540 | AA160507 | g1735874 | Hs.195850 | keratin 5 (epidermolysis bullosa simplex, Dowling-Meara/Kobner/Weber-Cockayne types) | KRT5 | Sensitivity |
| 592540 | AA160595 | g1735963 | Hs.195850 | keratin 5 (epidermolysis bullosa simplex, Dowling-Meara/Kobner/Weber-Cockayne types) | KRT5 | Sensitivity |
| 595037 | AA173872 | g1754021 | Hs.194691 | retinoic acid induced 3 | RAI3 | Sensitivity |
| 595037 | AA172400 | g1751448 | Hs.194691 | retinoic acid induced 3 | RAI3 | Sensitivity |
| 713263 | AA283106 | g1926031 | Hs.89040 | prepronociceptin | PNOC | Resistance |
| 713263 | AA283020 | g1925944 | Hs.89040 | prepronociceptin | PNOC | Resistance |
| 730871 | AA417025 | g2077124 | Hs.98186 | chromosome 21 open reading frame 22 | C21ORF22 | Sensitivity |
| 731311 | AA416767 | g2077721 | Hs.270266 | ESTs, Weakly similar to ORF YKL201c [*S. cerevisiae*] | — | Resistance |
| 739193 | AA421218 | g2100043 | Hs.7678 | cellular retinoic acid-binding protein 1 | CRABP1 | Sensitivity |
| 739193 | AA421217 | g2100042 | Hs.7678 | cellular retinoic acid-binding protein 1 | CRABP1 | Sensitivity |
| 741067 | AA478436 | g2207070 | Hs.250581 | SWI/SNF related, matrix associated, actin dependent regulator of chromatin, subfamily d, member 2 | SMARCD2 | Sensitivity |
| 741067 | AA402352 | g2056264 | Hs.250581 | SWI/SNF related, matrix associated, actin dependent regulator of chromatin, subfamily d, member 2 | SMARCD2 | Sensitivity |
| 741891 | AA402117 | g2056108 | Hs.170160 | RAB2, member RAS oncogene family-like | RAB2L | Sensitivity |
| 741891 | AA401972 | g2056031 | Hs.170160 | RAB2, member RAS oncogene family-like | RAB2L | Sensitivity |
| 743465 | AA609385 | g2457813 | Hs.112703 | ESTs | — | Sensitivity |
| 753587 | AA478585 | g2207219 | Hs.167741 | butyrophilin, subfamily 3, member A3 | BTN3A3 | Sensitivity |
| 753587 | AA479322 | g2207878 | Hs.167741 | butyrophilin, subfamily 3, member A3 | BTN3A3 | Sensitivity |
| 755881 | AA496539 | g2229860 | Hs.179902 | putative human HLA class II associated protein I | PHAP1 | Sensitivity |
| 756463 | AA481344 | g2210896 | Hs.8022 | downregulated in renal cell carcinoma | TU3A | Sensitivity |
| 756463 | AA436401 | g2141315 | Hs.8022 | downregulated in renal cell carcinoma | TU3A | Sensitivity |
| 759163 | AA442695 | g2154573 | Hs.118223 | microfibrillar-associated protein 4 | MFAP4 | Resistance |
| 759163 | AA496022 | g2229343 | Hs.118223 | microfibrillar-associated protein 4 | MFAP4 | Resistance |
| 767993 | AA418945 | g2080755 | Hs.29759 | RNA POLYMERASE I AND TRANSCRIPT RELEASE FACTOR | PTRF | Resistance |
| 767993 | AA418829 | g2080630 | Hs.29759 | RNA POLYMERASE I AND TRANSCRIPT RELEASE FACTOR | PTRF | Resistance |
| 768602 | AA425126 | g2107197 | Hs.98402 | ESTs | — | Sensitivity |
| 772446 | AA405640 | g2063132 | Hs.105915 | ESTs | — | Resistance |
| 772446 | AA405488 | g2063071 | Hs.105915 | ESTs | — | Resistance |
| 783729 | AA446928 | g2159593 | Hs.173664 | v-erb-b2 avian erythroblastic leukemia viral oncogene homolog 2 (neuro/glioblastoma derived oncogene homolog) | ERBB2 | Sensitivity |
| 783729 | AA443351 | g2156026 | Hs.173664 | v-erb-b2 avian erythroblastic leukemia viral oncogene homolog 2 (neuro/glioblastoma derived oncogene homolog) | ERBB2 | Sensitivity |
| 785847 | AA449119 | g2163139 | Hs.200478 | ubiquitin-conjugating enzyme E2M (homologous to yeast UBC12) | UBE2M | Resistance |
| 788234 | AA454080 | g2167749 | Hs.34853 | inhibitor of DNA binding 4, dominant negative helix-loop-helix protein | ID4 | Sensitivity |
| 788234 | AA452493 | g2166162 | Hs.34853 | inhibitor of DNA binding 4, dominant negative helix-loop-helix protein | ID4 | Sensitivity |

TABLE 1-continued

| Image Clone ID | Accession No. | Nuc Seq Id | Cluster Id | Cluster Title | Gene | Sensitivity or Resistance |
|---|---|---|---|---|---|---|
| 788524 | AA452937 | g2166606 | Hs.99291 | ESTs, Weakly similar to KIAA1006 protein [*H. sapiens*] | — | Resistance |
| 788524 | AA452801 | g2166470 | Hs.99291 | ESTs, Weakly similar to KIAA1006 protein [*H. sapiens*] | — | Resistance |
| 788609 | AA452899 | g2166568 | Hs.213586 | ESTs, Weakly similar to similar to KIAA0766 [*H. sapiens*] | — | Resistance |
| 789369 | AA464856 | g2189740 | Hs.34853 | inhibitor of DNA binding 4, dominant negative helix-loop-helix protein | ID4 | Sensitivity |
| 789369 | AA453341 | g2167010 | Hs.34853 | inhibitor of DNA binding 4, dominant negative helix-loop-helix protein | ID4 | Sensitivity |
| 795378 | AA453495 | g2167164 | Hs.236463 | *Homo sapiens* mRNA; cDNA DKFZp586I0521 (from clone DKFZp586I0521) | — | Sensitivity |
| 809694 | AA454702 | g2177478 | Hs.7678 | cellular retinoic acid-binding protein 1 | CRABP1 | Sensitivity |
| 809694 | AA456351 | g2178927 | Hs.7678 | cellular retinoic acid-binding protein 1 | CRABP1 | Sensitivity |
| 809998 | AA455195 | g2177971 | Hs.274376 | amylase, alpha 1A; salivary | AMY1A | Sensitivity |
| 809998 | AA454854 | g2177630 | Hs.75733 | amylase, alpha 2B; pancreatic | AMY2B | Sensitivity |
| 810871 | AA458981 | g2183888 | Hs.171814 | parathymosin | PTMS | Resistance |
| 810871 | AA459196 | g2184103 | Hs.171814 | parathymosin | PTMS | Resistance |
| 814297 | AA459105 | g2184012 | Hs.73947 | peptidase D | PEPD | Resistance |
| 814297 | AA459325 | g2184232 | Hs.73947 | peptidase D | PEPD | Resistance |
| 815284 | AA481608 | g2211160 | Hs.73947 | peptidase D | PEPD | Resistance |
| 815284 | AA481543 | g2211095 | Hs.73947 | peptidase D | PEPD | Resistance |
| 837891 | AA434092 | g2139006 | Hs.271869 | ESTs | — | Sensitivity |
| 837891 | AA434363 | g2139277 | Hs.243010 | ESTs, Moderately similar to GTP-BINDING PROTEIN TC10 [*H. sapiens*] | — | Sensitivity |
| 841679 | AA488699 | g2218301 | Hs.10803 | calcium and integring binding protein (DNA-dependent protein kinase interacting protein) | SIP2-28 | Sensitivity |
| 841679 | AA487575 | g2217739 | Hs.10803 | calcium and integring binding protein (DNA-dependent protein kinase interacting protein) | SIP2-28 | Sensitivity |
| 842863 | AA486403 | g2216567 | Hs.75789 | N-myc downstream regulated | NDRG1 | Sensitivity |
| 842863 | AA489261 | g2218863 | Hs.75789 | N-myc downstream regulated | NDRG1 | Sensitivity |
| 845658 | AA670144 | g2631643 | Hs.61762 | ESTs | — | Sensitivity |
| 859586 | AA668681 | g2630180 | Hs.278736 | cell division cycle 42 (GTP-binding protein, 25 kD) | CDC42 | Resistance |
| 859761 | AA668508 | g2630007 | Hs.183986 | poliovirus receptor-related 2 (herpesvirus entry mediator B) | PVRL2 | Resistance |
| 859858 | AA679454 | g2659976 | Hs.3132 | steroidogenic acute regulatory protein | STAR | Resistance |
| 897597 | AA496846 | g2230167 | Hs.278518 | DKFZP434D174 protein | DKFZP434D174 | Sensitivity |
| 897597 | AA496888 | g2230209 | Hs.19614 | gemin4 | GEMIN4 | Sensitivity |
| 897641 | AA496741 | g2230062 | Hs.103804 | heterogeneous nuclear ribonucleoprotein U (scaffold attachment factor A) | HNRPU | Sensitivity |
| 897641 | AA496792 | g2230113 | Hs.139572 | EST | — | Sensitivity |
| 969769 | AA772904 | g2825746 | Hs.132884 | heparan sulfate 6-O-sulfotransferase | HS6ST | Resistance |
| 970649 | AA774724 | g2834058 | Hs.25615 | YDD19 protein | YDD19 | Resistance |
| 1055543 | AA620821 | g2524760 | Hs.112911 | EST | — | Sensitivity |
| 1412238 | AA844818 | g2931269 | Hs.278399 | amylase, alpha 2A; pancreatic | AMY2A | Sensitivity |
| 1412245 | AA844831 | g2931282 | Hs.89717 | carboxypeptidase A2 (pancreatic) | CPA2 | Sensitivity |
| 1456937 | AA863449 | g2955928 | Hs.1154 | oviductal glycoprotein 1, 120 kD | OVGP1 | Resistance |
| 1470220 | AA865960 | g2958236 | Hs.127286 | ESTs | — | Resistance |
| 1473682 | AA916726 | g3056118 | Hs.125262 | DKFZP586G1624 protein | DKFZP586G1624 | Sensitivity |
| 1475842 | AA872143 | g2968321 | Hs.17820 | Rho-associated, coiled-coil containing protein kinase 1 | ROCK1 | Resistance |
| 1486028 | AA912032 | g3051424 | Hs.181059 | ESTs | — | Resistance |
| 1493205 | AA878923 | g2987888 | Hs.90680 | ESTs, Weakly similar to WD40 protein Ciao 1 [*H. sapiens*] | — | Resistance |
| 1550776 | AA912448 | g3051840 | Hs.121529 | ELK3, ETS-domain protein (SRF accessory protein 2) | ELK3 | Resistance |
| 1550909 | AA913206 | g3052598 | Hs.278606 | G antigen 7 | GAGE7 | Resistance |
| 1573946 | AA938494 | g3096522 | Hs.28555 | programmed cell death 9 | PDCD9 | Resistance |
| 1574438 | AA954935 | g3118630 | Hs.155324 | matrix metalloproteinase 11 (stromelysin 3) | MMP11 | Resistance |
| 1588935 | AA975612 | g3151404 | Hs.268557 | pleckstrin homology-like domain, family A, member 3 | PHLDA3 | Resistance |
| 1603560 | AA996122 | g3182611 | Hs.73947 | peptidase D | PEPD | Resistance |
| 1605142 | AA987928 | g3173292 | Hs.27457 | ESTs | — | Resistance |
| 1609538 | AI000966 | g3191520 | Hs.104696 | *Homo sapiens* mRNA for KIAA1324 protein, partial cds | — | Sensitivity |
| 1623016 | AI014781 | g3229117 | Hs.234903 | EST | — | Sensitivity |
| 1635203 | AI003775 | g3213285 | Hs.127824 | ESTs, Weakly similar to weak similarity to collagens [*C. elegans*] | — | Resistance |
| 1635978 | AI017801 | g3232137 | Hs.131201 | ESTs | — | Resistance |
| 1646649 | AI025974 | g3241587 | Hs.131678 | EST | — | Resistance |

TABLE 1-continued

| Image Clone ID | Accession No. | Nuc Seq Id | Cluster Id | Cluster Title | Gene | Sensitivity or Resistance |
|---|---|---|---|---|---|---|
| 1916700 | AI347629 | g4084835 | Hs.123107 | kallikrein 1, renal/pancreas/salivary | KLK1 | Resistance |
| 1946534 | AI351740 | g4088946 | Hs.890 | lymphotoxin beta (TNF superfamily, member 3) | LTB | Sensitivity |
| 1968246 | AI285751 | g3923984 | Hs.118722 | fucosyltransferase 8 (alpha (1,6) fucosyltransferase) | FUT8 | Resistance |

TABLE 2A

| EST | Sensitivity/Resistance | SEQ ID NO |
|---|---|---|
| cohXres112c05 | Sensitivity | 1 |
| jlhbab397f01 | Sensitivity | 18 |
| jlhbab412e01 | Sensitivity | 16 |
| jlhbab443e06 | Resistance | 2 |
| jlhbab453e07 | Sensitivity | 17 |
| jlhbac238e10 | Resistance | 3 |
| jlhbad283g07 | Resistance | 19 |
| jlhbae334b03 | Sensitivity | 4 |
| jMhXp229h07 | Resistance | 15 |
| jMhXp252a05 | Resistance | 5 |
| johOf009h09 | Resistance | 6 |
| johOf017b09 | Resistance | 7 |
| johOf021e06 | Resistance | 8 |
| johOf079g12 | Resistance | 9 |
| johOf083h04 | Resistance | 10 |
| johOf092b09 | Resistance | 11 |
| johOf094e10 | Resistance | 12 |
| jrhob001h03 | Resistance | 13 |
| jrhoc127f11 | Resistance | 14 |

TABLE 2B

```
>cohXres112c05
AGGTACAAGCTTTTTTTTTTTTTTTTTTTTTTTTTTCCTACTGGA
ATCGTTNAATGNGTCTACTTNTTCCACNCATAATTATAAAAGAATAAGAA
TCGACAAAAATATTTTNTTTCCATAATATGTANAGGNGGTTGGTTTCTTT
TTTTTTTTTTTCTTTCTTTTAACTTTTTTTTTTTTTTTTTTTTTTT
GGGCTCNAAAGGGGGTAGNGGGGGTNCTNTAGGACCTGCCCG >jlhbab443e06
TTTATGAGAAAGCAGCTATTAAAGGTAGAGTGATTCAAGTCTATAAGGCA
ATTTATATTCTATATTTAGTTTTTCATTCTGAATAGACTGAAAAAATATA
TGAATTAGAAATTTATTTAAGACCATCTTTCTTTTGTTGCTTTTTTAAA
CATTTACTTTTGTTTAAGCCATAAGGATGCATAAATTATACAGGGGATGA
CCTTATGAGTAACATCAAGAGGTATTTGAGAAATAACAGAACACGTCTAG
AAATGTATGGTGGTAATATTAATCTATACATTTTTTGGCATGATTTGTAC
ATTGACATTGTATGAAATGAGCACACTGAGGGTTTTNGGTGGTACTGNC
GCATCCAAGGAGGTTGGGGAGAACTATATAAGAATGTNTTATAATGACTA
TTTTAAATAAAGTAAAA >jlhbac238e10
CGTGACTGAGGACAGTGAAAAGAGCCGACCTGGTGTAGAGTGCTCATTTT
AGGTGCCAAGAAAAGCCTAATTTATTTTCAGGGCAAAACTTCTGCACTAG
GACAAATGTCTTCATTATAATCCAAAAGCAGCATCAGGAAAAGAAGCTGA
ACTGTGCGAATAGAAATGAATGGGGCTGCTGCTGCTGCTGCTTTCTT
TTTAATCAGTAGAAATGGAATTCTGCCTGCCAAACAGAAGTCTAGGAGGA
ACCTGCAGACGGGCCCTGTACTGAGGGCATTTTGTCAGGGCTTAAAGCAA
CCTTCAAGATCATGACACTCTGCTATGAGGACCGAAAGAACTTGGAGATA
AATATACATGTACTATGTGGTGGGACCGATTTTGAATCTGAACTAAATTA
AATGATGGAAAACGACCTTGGGTGAGTTCATTCATGGCTGAACTTGCTGG
GAATGATACAACTTTTCAAAATAATTTGTTTCCTTCAAATGACACCAACA
CCTATAGTTAAG >jlhbae334b03
NCGGTTGAACTACGGANAACAACNCGCTGCCTTCACAGNACCTAGAGTCT
CCTTTGGAGCTACGAACCTCGCCGAAGGTACGGCGACACAGACGNGANGT
GTACAAGCTTTTNTANATGGTGGATATTCNACAATTAAATTCNTACGTAC
TCNNNGTCCAGTCNNGAGTCCNANTGAGCTGTTTGCTAANTNATGAANTT
CNTTCNNGCACGTGAAGGGCAAAGAGAAATAAGGGCCNACTTGCNNNAAG
GGNTTCCTCGCGCATTTAGGTATCAGGCTTACTTNAGTATGTATNGCCNN
```

TABLE 2B-continued

```
CNTCCGAGCGGGAGAGCCAAGGGTGTCGTATAAAATTNAAAGGAATAACA
TAAAAA

>jMhXp252a05
GTCGACCCCGCGTCCGCTTAGGGAAGTGCAATATTATAAGTATAGTAATG
ACNGCAGNNGAGAACCATAATGATGGCCTCCCCGGCAAAGAAGAACCAAC
CCGTGTTACGCCTGAGGTTGCAATTTTTTGAATTTTTGCAGTNAGACCCT
GGCGATGACCTTGACGAGTAGGNGATAAATTCCACATGCTTAGCGTNCCA
GTAATGGAACACTAGGCATAAATGGGTTATTAAAGTATCCANAATTAACA
TGCTTAGCTGTGACATTGGAAAGGCAATGTGTTTGCTGTGGCACACATAC
TANTAAATAATGACTGGTCCGAATTTGGTTTTCGTTTGTCTATTAAAGTC
AATTTACTAAGGCAGGGAGGGCCGAGAGCTGTGCTGTCCAGTTCAATAGC
CATGCGTGACTGCTAAGGACTTCCAAAGTGGNTAGTCCAATGTCAGGTAT
GCTGCAAGTGTCAAACACACACTGGATTTCAAAGACTAAANCCAAAAAAA
TGTNAAATCATCTNAATATTTTGGTTATACTCGGTTNAAGAAAATAAAAT
TATTTTTGCCTTTTATGTTTTTAAAAG

>johOf009h09
GGNCAGCACACTCTACAAAGGCAGTCAACTACATGACACATTCCGCTTCT
GCCTGGTCACCAACTTGACGATGGACTCCGTGTTGGTCACTGTCAAGGCA
TTGTTCTCCTCCAATTTGGACCCCAGCCTGGTGGAGCAAGTCTTTCTAGA
TAAGACCCTGAATGCCTCATTCCATTGGCTGGGCTCCACCTACCAGTTGG
TGGACATCCATGTGACAGAAATGGAGTCATCAGTTTATCAACCAACAAGC
AGCTCCAGCACCCAGCACTTCTACCTGAATTTCACCATCACCAACCTACC
ATATTCCCAGGACAAAGCCCAGCCAGGCACC >johOf017b09
CCCTCGCGGTGGCGGGCGAGGTGCATCACCCTGCTGAGGGACATCCAGGA
CAAGGTCACCACACTCTACAAAGGCAGTCAAGTACATGACACATTCCGCT
TCTGCCTGGTCACCAACTTGACGATGGACTCCGTGTTGGTCACTGTCAAG
GCATTGTTCTCCTCCAATTTGGACCCCAGCCTGGTGGAGCAAGTCTTTCT
AGATAAGACCCTGAATGCCTCATTCCATTGGCTGGGCTCCACCTACCAGT
TGGTGGACATCCATGTGACAGAAATGGAGTCATCAGTTTATCAACCAACA
AGCAGCTCCAGCACCCAGCACTTCTACCTGAATTTCACCATCACCAACCT
ACGATATTCCCAGGACAAAGCCCAGCCAGGCACCACCAATTACCAGAGGA
ACAAAAGGAATATTGAGGATGCGCTCAACCAACTGTTCGAAACAGC >johOf021e06
TACTTAGGGCGAATTGGAGCTCGGCGCGGTGGGGCCGAGGTAGGGGGGA
GATAAGAGCCTGAATGCCTCATTCCATTGGGTGGGCTCGACGTACCAGTT
GGTGGACATCCATGTGACAGAAATGGAGTCATCAGTTTATCAACCAACAA
GCAGCTCCAGCACGGAGCACTTCTACCTGAATTTCACCATCACCAACCTA
CCATATTCCCGGGACAAAGCCCAGCCAGGCACCACCAATTACCAGAGGAA
CAAAAGGAATATTGAGGATGCGCTCAACCAACTCTTCCGAAACAGCAGCA
TCAAGAGTTATTTTTCTGACTGTCAAGTTTCAACATTCAGGTCTGTCCCC
AACAGGGACCCACACCGGGGTGGACTCCCTGTGTAACTTCTCGCCACTGGC
TCGAGAGTAGACAGAGTTGCCATCTATGAGGAATTTGTGCGGATGACCC
GGAATGGGTACCTGCCCGGGCCGGCCGCTTCGGCTTTAGAACTAGTN >johOf079g12
ATAGGGCGAATTGGAGCTCCCCGCGGNGGCGGCCGAGGTACCATTCCGGG
TCATCCGCAGAAATTCCTCATAGATGGCAACTCTGTCTACTCTCCGAGCC
AGTGGCGAGAAGTTACACAGGGAGTCCACCCCGGTGTGGTGCCTGTTGGG
GACAGACCTGAATGTTGAAACTTGACAGTCAGAAAAATAACTCTTGATGC
TGCTGTTTCGGAAGAGTTGGTTGAGCGGATCGTCAATATTCCTTTTGTTC
CTCTGGTAATTGGTGGTGCCTGGCTGGGCTTTGTCCTGGGAATATGGTAG
GTTGGTGATGGTGAAATTCAGGTAGAAGTGCTGGGTGCTGGAGCTGCTTG
TTGGTTGATAAACTGATGACTCCATTTCTGTCACATGGATGTCCACCAAC
TGGTAGGTGGAGCGCAGCCAATGGGAATGAGGCATTCAGGGTCTTATCTA
GAAAGAGTTGGTCCACCAGGCTGGGGTCCAAATTGGAG >johOf083h04
CCGCGGTGGCGGCCGCGCGGGCAGGTACATCACCCTGCTGAGGGACATCC
AGGACAAGGTCACCACACTCTACAAAGGCAGTCAACTACATGACAGATTC
```

TABLE 2B-continued

```
GGCTTCTGCCTGGTCACCAACTTGACGATGGACTCCGTGTCGGTCACTGT
CAAGGCATTGTTCTCCTCCAATTTGGACCCCAGCCTGGTGGAGCAAGTCT
TTCTAGATAAGACCCTGAATGCCTCATTCCATTGGCTGGGCTCCACCTAC
CAGTTGGTGGACATCCATGTGGCAGAAATGGAGTCATCAGTTTATCAACC
AACAAGCAGCTCCAGCACCCAGCACTTCTACCTGAATTTCACCATCACCA
ACCTACCATATTCCCAGGACAAAGCCCAGCCAGGCACCACCAATTACCAG
AGGAAGAAAAGGAATATTGAGGATGCGCTCAACGAACTCTTCCGAAACAG
CAGCATCAAGAGT

>johOf092b09
ACCGCNGTGGCGGCCGCCCGGGCAGGTACATCACCCTGCTGAGGGACTTT
TNNGGACAAGGTCACCACACTCTACAAAGGCAGTCAACTACATGAAGCAT
TCCGCTTCTGCCTGGTCACCAACTTGACGATGGACTCCGTGTTGGTCACT
GTCAAGGCATTGTTCTCCTCCAATTTGGACCCCAGCCTGGTGGAGCAAGT
CTTTCTAGATAAGACCCTGAATGCCTCATTCCATTGGCTGGGCTCCACCT
ACCAGTTGGTGGACATCCATGTGACAGAAATGGAGTCATCAGTTTTATCA
AC >johOf094e10
AGGGCGAATTGGAGCTCNCCGCGGTGGCGGCCGAGGTACCACCTGAAGGC
CCTCACACTCAACTTCACCATCTCCAATCTCCAGTATTCAGCAGATATGG
GCAAGGGCTCAGCTACATTCAACTCCACCGAGGGGGTCCTTCAGCACCTG
CTCAGACCCTTGTTCCAGAAGAGCAGCATGGGCCCCTTCTACTTGGGTTG
CCAACTGATCTCCCTCAGGCCTGAGAAGGATGGGGCAGCCACTGGTGTGG
ACACCACCTGCACCTACCACCCTGACCCTGTGGGCCCCGGGCTGGACATA
CAGCAGCTTTACTGGGAGCTGAGTCAGCTGACCCATGGGTGTCACCCAAC
TGGGCTTCTATTGTCCTGGACAGGGATAGCCTCTTCATCAATGGCTATGC
ACCCCAAAATTTATCAATCCGGGGCGAGGTACCTGCCCCGGGCGGGCCG
CTTAAAACTAGGNGGGATCCCCCNGGCTTGCAGGAATTTCGATATTGAAG
CTTATCGATAGCCGTCGNACCTTCGAGGGGGGGG >jrhob001h03
TGGGGGAAAGGGAGNNCCCAACGATCCTGGAACTTTAANTNTGGAAAGAG
TGAGATTCAGAAATCGCCACNACTGGACTTTAAGGGACGTCCTGTGTCAG
CACAANGGACTGGCACACACAGACACACNAGACCGANGANAAACTGCANA
CAAATGGAGATACNAANACTTAGAAGGACAGCTCCTTTCACCTCATCCTA
CTTGTCCAGAAGGTAAAAGACACANCCAGAAAGAAAAGGCATCNGCTCA
NCTCTCAGATCANGACANGCTGTGGATCTGTGGCGGTACT >jrhoc127f11
GGGTCCGAATTTCCTGGGTACCCCGTATATAAGAAAATGTTAAAGTCAGG
CAGGAAAATATAGAATTAAAGGCTTATAGTATATTATATAGNAAAGCCG
TATATAGTATAGACAGAAAAGTTTAGGGAAGGCCCACAATTGCAAAGAAA
AGTGGTGGTCACGGAACAAGGGAATGTCATACAAATGTGGACACACACTG
CGTTACTGAGCGCACGTCTCATAGGTGAGAAGCATACTCTAGAAGGTG
AGAAATGAGAATTTTCACTTCCATCCTTCCATTTGTTGTGTGACTCTGCC
ATTTACTTTCCTTTNTTTTGTATTTTCATTTTGGTTTTAAAAATGGAAAT
ATGAATTTTGAATTTCTGCTCTATCTCACAGGTTTTTTGTGGGGATGCAT
TTAAAANGTTTAATTAGTAAATAATGGTAT >jMhXp229h07
CCAAACTATTTGGACAGAATGGCTTCAAAAGCTAGGCGNAAATGTTCACA
TTATAAAAGTTAAATATTACCTTCAATACCTGTCAGTAGCCTACTGACA
AATTATGACTAAACAAAGGTATTTGTATGACTATGTAATAGATCATGCTG
TGAAAAGTAAACAAATAACAAAAAAAAACTTGTCCTAATGGGAAAGCATG
CTTAATAAAAGGAAATGCACGAAGTTATAAACATGTTTTGTNAGTAAGTA
TTCAGAATTAAAATTATGTGATACATTTTTATGATTGCTTAATGATCCTT
GGATGTCAGATTCCTTGGATTCTAATTTATAGCTAAATTATAATGAAAATT
CAAGGCTTGGTGNAGCAACTCTGTCAACAAATATATTAGTTTNGGTTATA
TATNTNGATTCNTTATGTGGGAAAAATTACTACCC >jlhbab412e01
CGGCCGGCCCGGGGATGCCGAGTCCCAAGAGGCCGAGTTTGAGAGGCTG
GTGGCAGAATTCCCGGAGAAGGAGGCCCAGCTGTCCCTGGTGGAAGCGCA
GGGCTGGCTGGTGATGGAGAAGTCTTCTCCGGAGGGTGCTGCCGTGGTGC
AGGAGGAGGTCAGGACGCTGGCAGAGTCGTGGCGGGCCTTGAGCTGCTG
GAAGAAAGTCTGCTGAGCCTCATCAGAAACTGGCATCTGCAGAGGATGGA
AGTGGATTCGGGAAGAAAATGGTTTTCACCAACAACATCCCAAAGTCAG
GATTTCTCATCAATCCCATGGATCCTATTCGCAGGCATCGTGGACGGGTG
AGTGTGTCTAGCAGGGCTGTGGGAGAAGGGGCCAGGCCCCAGGTCAAGAG
GTGGGTAGGGGTCTCGACACAGGCCCCTCCCTGTGTGGGGCAACATGCT
CTGGTCTGAGGACTTGGCCACGTCCTGTCTCATTTGAGCCTGC >jlhbab453e07
GCGTCCGGTTACAAAGTCAGGTTGTTATGGTTTGCATGACTTTGAGAAGC
TAGTGGAATGGAAATAAAGTTAGGAGCAGCAGGAGGAGGCTCTGTGTGGG
CACATCTCCTTCAGGGGCATGGTACTGTTCATGGACAGAGGAAGTCCTAT
GGCATATGCTGGGACAGACAGTGAAGGGTAGGTCTTACAAAGAGGCTTTA
CGTTAGAGTATAATAATCACTTATCTGTATGCATCTATGAATGATCTCAC
CGGATGTGAAGAATATGTATTTTTAAAAACAGCATGAAACGGCCTGTAAT
CCCAGTACTTTTGGG >jlhbab397f01
ACTTATTGAATCATCGAATTCATTGAAGTTTGGCTCCAACCTATCATATC
GCCGATGTTTACTTTTTCCTATTCTTCATAAAGTTCTAAATTCAGAATGT
GAGGTGGACAAATTCATTTCAGTTCCACAAGTGGTAGCATTTAAATATCA
GCAGCTTAAGTATTCAAAATTAATAGATTGCATTTTTAAAATGGTGAAAT
TCTGACAGTTTGCAGGGAAAAGGTGCTGAATATCTTGATATAATTTACAT
ACTTCTATAAACAGGCATTTTTATACCTTTGGAAAGATAAATGAGTAGAA
ACCAAGTATTTTACAATTCTAATAGTTATACTGACATGT jlhbad2B3g07
TCCGCTAAAATTTGTTCGGGCCTTTGGCTTAATTCAGAGATCTGCCCAT
GGGGTTCTATTACTTTGCTCTTTAACTTTGTTCGATCCTTCTTGGATCAG
TCTTGCAATTCATTCTTGTCTTTTCCTGAATAACATCTATGTTTTGCCCT
CTTTTGAGTGCTATCTTAAATATGCCAGCCTATTTCGTACCTTTCTTGTGCA
GGGTAGCATAATTTTTACTTTCCATTATACCTCAGTCCCACACCTTGTTG
TCTGTTTATTTCAATACCTAAGTATTTATCCTCAGTTCCTAGCTTACTT
TAGTTCTGAAAGTTGGATATCCATAATTGTAGTGGTCTTAAATCTGTAAA
ACACATATGGATGGGAAACCACTGAATAATGTAAATAAATATGAATAACG
ATGATAAAATAAAAATGATAAAAATAACTGAGTTCAATGATATTAAAAAC
ATAAGTCA
```

TABLE 3A

| Clone | Annotation |
|---|---|
| 242642 | EST//(Hs.42041;) |
| 121561 | ESTs//(Hs.226410;) |
| 32567 | inhibitor of DNA binding 4, dominant negative helix-loop-helix protein//(Hs.34853; NM_001546) |
| 788234 | inhibitor of DNA binding 4, dominant negative helix-loop-helix protein//(Hs.34853; NM_001546) |
| 789369 | inhibitor of DNA binding 4, dominant negative helix-loop-helix protein//(Hs.34853; NM_001546) |
| 27544 | prominin (mouse)-like 1//(Hs.112360; NM_006017) |
| 322723 | ESTs//(Hs.93231;) |
| 243741 | diubiquitin//(Hs.44532; NM_006398) |
| 1055543 | EST//(Hs.112911;) |
| 245330 | insulin-like growth factor 2 (somatomedin A)//(Hs.251664; NM_000612) |
| 1574438 | matrix metalloproteinase 11 (stromelysin 3)//(Hs.155324; NM_005940) |
| 234907 | KIAA0094 protein//(Hs.82007;) |
| 1456937 | oviductal glycoprotein 1, 120 kD//(Hs.1154; NM_002557) |
| 1493205 | ESTs, Weakly similar to WD40 protein Ciao 1 [*H. sapiens*]//(Hs.90680;) |
| 506583 | cardiotrophin 1//(Hs.25537; NM_001330) |
| jlhbac238e10 | |
| 970649 | ESTs//(Hs.116561;) |
| 291880 | microfibrillar-associated protein 27//(Hs.83551; NM_002403) |
| 731311 | ESTs, Weakly similar to ORF YKL201c [*S. cerevisiae*]//(Hs.270266;) |
| 1588935 | ESTs, Highly similar to TDAG51/lpl homologue 1 [*H. sapiens*]//(Hs.110222;) |
| 859586 | cell division cycle 42 (GTP-binding protein, 25 kD)//(Hs.146409; NM_001791) |
| 1550909 | G antigen 7//(Hs.184794;) |
| 810871 | parathymosin//(Hs.171814; NM_002824) |
| 159455 | similar to vaccinia virus HindIII K4L ORF//(Hs.74573;) |
| jlhbad283g07 | |
| 814297 | peptidase D//(Hs.73947; NM_000285) |
| 1635978 | ESTs//(Hs.131201;) |
| 785847 | ubiquitin-conjugating enzyme E2M (homologous to yeast UBC12)//(Hs.200478; NM_003969) |
| 274677 | ESTs//(Hs.169338;) |
| 859761 | Untitled//(Hs.270880;) |
| 377799 | cyclin A1//(Hs.79378; NM_003914) |
| 713263 | prepronociceptin//(Hs.89040;) |
| 1916700 | kallikrein 1, renal/pancreas/salivary//(Hs.123107; NM_002257) |
| 490600 | FOS-like antigen 2//(Hs.155210; NM_005253) |

TABLE 3B

| Clone | Annotation |
|---|---|
| 1916700 | kallikrein 1, renal/pancreas/salivary//(Hs.123107; NM_002257) |
| 490600 | FOS-like antigen 2//(Hs.155210; NM_005253) |
| johOf021e06 | |
| 859761 | Untitled//(Hs.270880;) |
| 814297 | peptidase D//(Hs.73947; NM_000285) |
| johOf009h09 | |
| 1605142 | ESTs//(Hs.27457;) |
| johOf017b09 | |
| johOf092b09 | |
| johOf083h04 | |
| 451706 | polymerase (DNA directed), alpha//(Hs.267289;) |
| 506583 | cardiotrophin 1//(Hs.25537; NM_001330) |
| 753587 | butyrophilin, subfamily 3, member A3//(Hs.167741; NM_006994) |
| 789369 | inhibitor of DNA binding 4, dominant negative helix-loop-helix protein//(Hs.34853; NM_001546) |
| 261828 | UNIGENE-ambiguity: Hs.226216::Hs.270258! ESTs//(Hs.226216;) |
| 969769 | heparan sulfate 6-O-sulfotransferase//(Hs.132884; NM_004807) |
| 1603560 | peptidase D//(Hs.73947; NM_000285) |
| 32567 | inhibitor of DNA binding 4, dominant negative helix-loop-helix protein//(Hs.34853; NM_001546) |
| 772446 | ESTs//(Hs.105915;) |
| 159455 | similar to vaccinia virus HindIII K4L ORF//(Hs.74573;) |
| 788234 | inhibitor of DNA binding 4, dominant negative helix-loop-helix protein//(Hs.34853; NM_001546) |
| johOf094e10 | |
| 897597 | DKFZP434B131 protein//(Hs.19614;) |
| 810871 | parathymosin//(Hs.171814; NM_002824) |
| 731311 | ESTs, Weakly similar to ORF YKL201c [S. cerevisiae]//(Hs.270266;) |
| 753587 | butyrophilin, subfamily 3, member A3//(Hs.167741; NM_006994) |
| 322443 | ESTs//(Hs.238927;) |
| 66498 | ESTs//(Hs.21688;) |
| 242642 | EST//(Hs.42041;) |
| 970649 | ESTs//(Hs.116561;) |
| 841679 | calcium and integrin binding protein (DNA-dependent protein kinase interacting protein)//(Hs.10803;) |
| 1588935 | ESTs, Highly similar to TDAG51/lpl homologue 1 [H. sapiens]//(Hs.110222;) |
| 785847 | ubiquitin-conjugating enzyme E2M (homologous to yeast UBC12)//(Hs.200478; NM_003969) |
| johOf079g12 | |
| 121661 | ESTs//(Hs.226410;) |

TABLE 4

| Clone | Annotation |
|---|---|
| 66420 | ESTs//(Hs.189713;) |
| 460487 | lactotransferrin//(Hs.347; NM_002343) |
| cohXres112c05 | |
| 242642 | EST//(Hs.42041;) |
| 430077 | aminolevulinate, delta-, synthase 2 (sideroblastic/hypochromic anemia)//(Hs.79103; NM_000032) |
| 1623016 | EST//(Hs.234903;) |
| 27544 | prominin (mouse)-like 1//(Hs.112360; NM_006017) |
| 121661 | ESTs//(Hs.226410;) |
| 324699 | Homo sapiens clone 23551 mRNA sequence//(Hs.184019;) |
| 199243 | EST//(Hs.35467;) |
| 741067 | UNIGENE-ambiguity: Hs.250581::Hs.69469! SWI/SNF related, matrix associated, actin dependent regulator of chromatin, subfamily d, member 2//(Hs.250581; NM_003077) |
| 127192 | ESTs//(Hs.20131;) |
| 1055543 | EST//(Hs.112911;) |
| 344942 | protein tyrosine phosphatase, receptor type, f polypeptide (PTPRF), interacting protein (liprin), alpha 3//(Hs.109299;) |

TABLE 4-continued

| Clone | Annotation |
|---|---|
| 154172 | IgG Fc binding protein//(Hs.111732; NM_003890) |
| 756463 | downregulated in renal cell carcinoma//(Hs.8022; NM_007177) |
| 277173 | laminin receptor 1 (67 kD, ribosomal protein SA)//(Hs.181357; NM_002295) |
| 489637 | ESTs//(Hs.22793;) |
| 743465 | ESTs//(Hs.112703;) |
| 755881 | ESTs//(Hs.179902;) |
| 595037 | retinoic acid induced 3//(Hs.194691; NM_003979) |
| 66317 | H1 histone family, member 2//(Hs.7644; NM_005319) |
| 795378 | ESTs//(Hs.236463;) |
| 1035784 | |
| 344958 | ESTs//(Hs.214507;) |
| 436782 | ESTs//(Hs.124778;) |
| 730871 | ESTs//(Hs.98186;) |
| 298417 | trefoil factor 3 (intestinal)//(Hs.82961; NM_003226) |
| 845658 | ESTs//(Hs.61762;) |
| 510576 | UNIGENE-ambiguity: Hs.122576::Hs.91011! ESTs//(Hs.122576;) |
| 203348 | ESTs//(Hs.9829;) |
| 783729 | v-erb-b2 avian erythroblastic leukemia viral oncogene homolog 2 (neuro/glioblastoma derived oncogene homolog)//(Hs.173664; NM_004448) |
| 241120 | |
| 768602 | ESTs//(Hs.98402;) |
| 51221 | ortholog of rat pippin//(Hs.106635;) |
| 897641 | UNIGENE-ambiguity: Hs.103804::Hs.139572! heterogeneous nuclear ribonucleoprotein U (scaffold attachment factor A)//(Hs.103804; NM_004501) |
| 436348 | ESTs, Weakly similar to apoptotic protease activating factor 1 [M. musculus]//(Hs.122614;) |
| 295723 | ESTs//(Hs.49275;) |
| 592540 | keratin 5 (epidermolysis bullosa simplex, Dowling-Meara/Kobner/Weber-Cockayne types)//(Hs.195850; NM_000424) |
| 970649 | ESTs//(Hs.116561;) |
| 1456937 | oviductal glycoprotein 1, 120 kD//(Hs.1154; NM_002557) |
| 1493205 | ESTs, Weakly similar to WD40 protein Ciao 1 [H. sapiens]//(Hs.90680;) |
| 1573946 | ESTs, Weakly similar to B0511.8 [C. elegans]//(Hs.28555;) |
| 1470220 | ESTs//(Hs.127286;) |
| 785847 | ubiquitin-conjugating enzyme E2M (homologous to yeast UBC12)//(Hs.200478; NM_003969) |
| 461468 | ESTs//(Hs.163036;) |
| 33267 | insulin-like growth factor binding protein 2 (36 kD)//(Hs.162;) |
| 506516 | ESTs//(Hs.120152;) |
| 1486028 | ESTs//(Hs.181059;) |
| 1550776 | ELK3, ETS-domain protein (SRF accessory protein 2) NOTE: Symbol and name provisional.//(Hs.121529; NM_005230) |
| 154929 | |
| 1475842 | Rho-associated, coiled-coil containing protein kinase 1//(Hs.17820; NM_005406) |
| 26617 | activated leucocyte cell adhesion molecule//(Hs.10247; NM_001627) |
| jMhXp252a05 | |
| 1646649 | EST//(Hs.131678;) |
| 1968246 | fucosyltransferase 8 (alpha (1,6) fucosyltransferase)//(Hs.118722; NM_004480) |
| 153505 | dermatopontin//(Hs.80552; NM_001937) |
| jlhbab443e06 | |
| 969769 | heparan sulfate 6-O-sulfotransferase//(Hs.132884; NM_004807) |
| 1635203 | ESTs, Weakly similar to weak similarity to collagens [C. elegans]//(Hs.127824;) |
| 814297 | peptidase D//(Hs.73947; NM_000285) |
| 1916700 | kallikrein 1, renal/pancreas/salivary//(Hs.123107; NM_002257) |
| 859858 | steroidogenic acute regulatory protein//(Hs.3132; NM_000349) |
| 810871 | parathymosin//(Hs.171814; NM_002824) |

TABLE 5

| Clone | Annotation |
|---|---|
| 242642 | EST//(Hs.42041;) |
| 121661 | ESTs//(Hs.226410;) |
| 739193 | cellular retinoic acid-binding protein 1//(Hs.7678; NM_004378) |
| 32567 | inhibitor of DNA binding 4, dominant negative helix-loop-helix protein//(Hs.34853; NM_001546) |
| 788234 | inhibitor of DNA binding 4, dominant negative helix-loop-helix protein//(Hs.34853; NM_001546) |
| 809694 | cellular retinoic acid-binding protein 1//(Hs.7678; NM_004378) |
| 27544 | prominin (mouse)-like 1//(Hs.112360; NM_006017) |
| 809998 | UNIGENE-ambiguity: Hs.252475::Hs.250817! amylase, alpha 2B; pancreatic//(Hs.252475;) |
| 789369 | inhibitor of DNA binding 4, dominant negative helix-loop-helix protein//(Hs.34853; NM_001546) |
| 1412238 | amylase, alpha 2A; pancreatic//(Hs.75733; NM_000699) |
| 755881 | ESTs//(Hs.179902;) |
| 743465 | ESTs//(Hs.112703;) |
| 460487 | lactotransferrin//(Hs.347; NM_002343) |
| 1609538 | ESTs//(Hs.104696;) |
| 298417 | trefoil factor 3 (intestinal)//(Hs.82961; NM_003226) |
| 1412245 | carboxypeptidase A2 (pancreatic)//(Hs.89717; NM_001869) |
| 322723 | ESTs//(Hs.93231;) |
| jlhbab397f01 | |
| jlhbae334b03 | |
| 154654 | ESTs, Highly similar to IROQUOIS-CLASS HOMEODOMAIN PROTEIN IRX-3 [*M. musculus*]//(Hs.3321;) |
| 842863 | N-myc downstream regulated//(Hs.75789; NM_006096) |
| 1473682 | DKFZP586G1624 protein//(Hs.125262;) |
| 285507 | EST//(Hs.161495;) |
| 277173 | laminin receptor 1 (67 kD, ribosomal protein SA)//(Hs.181357; NM_002295) |
| jlhbab453e07 | |
| 488945 | UNIGENE-ambiguity: Hs.252475::Hs.180149! amylase, alpha 2B; pancreatic//(Hs.252475;) |
| jlhbab412e01 | |
| 741891 | RAB2, member RAS oncogene family-like//(Hs.170160; NM_004761) |
| 122906 | ESTs//(Hs.186545;) |
| 1946534 | lymphotoxin beta (TNF superfamily, member 3)//(Hs.890; NM_002341) |
| 837891 | UNIGENE-ambiguity: Hs.271869::Hs.267654! ESTs//(Hs.271869;) |
| 1493205 | ESTs, Weakly similar to WD40 protein Ciao 1 [*H. sapiens*]//(Hs.90680;) |
| jrhoc127f11 | |
| jlhbac238e10 | |

TABLE 5-continued

| Clone | Annotation |
|---|---|
| 713263 | prepronociceptin//(Hs.89040;) |
| 970649 | ESTs//(Hs.116561;) |
| jlhbad283g07 | |
| 767993 | *Homo sapiens* mRNA; cDNA DKFZp586L2123 (from clone DKFZp586L2123)//(Hs.29759;) |
| 1456937 | oviductal glycoprotein 1, 120 kD//(Hs.1154; NM_002557) |
| 284220 | CD22 antigen//(Hs.171763; NM_001771) |
| 1635978 | ESTs//(Hs.131201;) |
| 731311 | ESTs, Weakly similar to ORF YKL201c [*S. cerevisiae*]//(Hs.270266;) |
| jMhXp229h07 | |
| 785847 | ubiquitin-conjugating enzyme E2M (homologous to yeast UBC12)//(Hs.200478; NM_003969) |
| 788524 | ESTs, Weakly similar to KIAA1006 protein [*H. sapiens*]//(Hs.99291;) |
| 759163 | microfibrillar-associated protein 4//(Hs.118223;) |
| 788609 | ESTs, Weakly similar to similar to KIAA0766 [*H. sapiens*]//(Hs.213586;) |
| 128126 | decay accelerating factor for complement (CD55, Cromer blood group system)//(Hs.1369;) |
| 1635203 | ESTs, Weakly similar to weak similarity to collagens [*C. elegans*]//(Hs.127824;) |
| 859858 | steroidogenic acute regulatory protein//(Hs.3132; NM_000349) |
| jrhob001h03 | |
| 431944 | ESTs//(Hs.117106;) |
| 815284 | peptidase D//(Hs.73947; NM_000285) |

TABLE 6

| Clone | Annotation |
|---|---|
| 242642 | EST//(Hs.42041;) |
| 32567 | inhibitor of DNA binding 4, dominant negative helix-loop-helix protein//(Hs.34853; NM_001546) |
| 788234 | inhibitor of DNA binding 4, dominant negative helix-loop-helix protein//(Hs.34853; NM_001546) |
| 789369 | inhibitor of DNA binding 4, dominant negative helix-loop-helix protein//(Hs.34853; NM_001546) |
| 814297 | peptidase D//(Hs.73947; NM_000285) |
| 859761 | Untitled//(Hs.270880;) |
| 1916700 | kallikrein 1, renal/pancreas/salivary//(Hs.123107; NM_002257) |
| 490600 | FOS-like antigen 2//(Hs.155210; NM_005253) |

---

What is claimed is:

1. A method for determining whether paclitaxel, cisplatin, or a combination of paclitaxel and cisplatin cannot be used to reduce the growth of an ovarian tumor, comprising the steps of:
   a) providing a sample of ovarian tumor cells;
   b) determining whether the tumor cells express one or more resistance markers selected from the group consisting of a jihbab443e06 mRNA comprising the RNA sequence corresponding to SEQ ID NO: 2; a jihbac238e10 mRNA comprising the RNA sequence corresponding to SEQ ID NO: 3; a jihbad283g07 mRNA marker comprising the RNA sequence corresponding to the nucleotide sequence of SEQ ID NO: 19, a jMhXp229h07mRNA comprising the RNA sequence corresponding to SEQ ID NO: 15, a jMhXp252a05 mRNA comprising the RNA sequence corresponding to SEQ ID NO: 5; a johOf009h09 mRNA comprising the RNA sequence corresponding to SEQ ID NO: 6; a johOf017b09 mRNA comprising the RNA sequence corresponding to SEQ ID NO: 7; a johOf021e06 mRNA comprising the RNA sequence corresponding to SEQ ID NO: 8; a johOf079g12 mRNA comprising the RNA sequence corresponding to SEQ ID NO: 9; a johOf083h04 mRNA comprising the RNA sequence corresponding to SEQ ID NO: 10; a johOf092b09 mRNA comprising the RNA sequence corresponding to SEQ ID NO: 11; a johOf094e10 mRNA comprising the RNA sequence corresponding to SEQ ID NO: 12; a jrhob001h03 mRNA comprising the RNA sequence corresponding to SEQ ID NO: 13, and a jrhoc127f11 mRNA comprising the RNA sequence corresponding to SEQ ID NO: 14, wherein at least one of the one or more resistance markers is a marker selected from the group consisting of a jihbad283g07 mRNA marker comprising the RNA sequence corresponding to the nucleotide sequence of SEQ ID NO: 19, a jMhXp229h07mRNA comprising the RNA sequence corresponding to SEQ ID NO: 15, and a jrhoc127f11 mRNA comprising the RNA sequence corresponding to SEQ ID NO: 14; and
   and c) determining that paclitaxel, cisplatin, or a combination of paclitaxel and cisplatin cannot be used to reduce the growth of the tumor when one or more of the resistance markers is expressed or overexpressed by the tumor cells.

2. The method of claim 1, wherein the ovarian tumor cells are obtained from an ovarian tumor cell line or an ovarian tumor obtained from a subject.

3. A method for determining whether paclitaxel, cisplatin, or a combination of paclitaxel and cisplatin can be used to reduce the growth of an ovarian tumor, comprising the steps of:
   a) providing a sample of ovarian tumor cells;
   b) determining whether the tumor cells express one or more resistance markers selected from the group consisting of a jihbab443e06 mRNA comprising the RNA sequence corresponding to SEQ ID NO: 2; a jihbac238e10 mRNA comprising the RNA sequence corresponding to SEQ ID NO: 3; a jihbad283q07 mRNA marker comprising the RNA sequence corresponding to the nucleotide sequence of SEQ ID NO: 19, a jMhXp229h07mRNA comprising the RNA sequence corresponding to SEQ ID NO: 15, a jMhXp252a05 mRNA comprising the RNA sequence corresponding to SEQ ID NO: 5; a johOf009h09 mRNA comprising the RNA sequence corresponding to SEQ ID NO: 6; a johOf017b09 mRNA comprising the RNA sequence corresponding to SEQ ID NO: 7; a johOf021e06 mRNA comprising the RNA sequence corresponding to SEQ ID NO: 8; a johOf079g12 mRNA comprising the RNA sequence corresponding to SEQ ID NO: 9; a johOf083h04 mRNA comprising the RNA sequence corresponding to SEQ ID NO: 10; a johOf092b09 mRNA comprising the RNA sequence corresponding to SEQ ID NO: 11; a johOf094e10 mRNA comprising the RNA sequence corresponding to SEQ ID NO: 12; a jrhob001h03 mRNA comprising the RNA sequence corresponding to SEQ ID NO: 13, and a jrhoc127f11 mRNA comprising the RNA sequence corresponding to SEQ ID NO: 14, wherein at least one of the one or more resistance markers is a marker selected from the group consisting of a jihbad283g07 mRNA marker comprising the RNA sequence corresponding to the nucleotide sequence of SEQ ID NO: 19, a jMhXp229h07mRNA comprising the RNA sequence corresponding to SEQ ID NO: 15, and a jrhoc127f11 mRNA comprising the RNA sequence corresponding to SEQ ID NO: 14; and
   c) determining that paclitaxel, cisplatin, or a combination of paclitaxel and cisplatin can be used to reduce the growth of the tumor when one or more of the resistance markers is not expressed by the tumor cells.

4. The method of claim 3, wherein the ovarian tumor cells are obtained from an ovarian tumor cell line or an ovarian tumor obtained from a subject.

* * * * *